United States Patent
Medina et al.

(10) Patent No.: US 6,284,923 B1
(45) Date of Patent: Sep. 4, 2001

(54) SUBSTITUTED BENZENE COMPOUNDS AS ANTIPROLIFERATIVE AND CHOLESTEROL LOWERING ACTION

(75) Inventors: Julio Cesar Medina, Belmont; David Louis Clark, Albany; John A. Flygare; Terry J. Rosen, both of Burlingame; Bei Shan, Foster City, all of CA (US)

(73) Assignee: Tularik INC, South San Francisco, CA (US)

( * ) Notice: Subject to any disclaimer, the term of this patent is extended or adjusted under 35 U.S.C. 154(b) by 0 days.

(21) Appl. No.: 08/917,025

(22) Filed: Aug. 22, 1997

(51) Int. Cl.$^7$ .......................... A61K 31/36; A61K 31/21; A61K 31/275; A61K 31/18

(52) U.S. Cl. ..................... 564/86; 514/466; 514/513; 514/524; 514/602; 514/603; 514/604; 549/439; 558/413; 562/12; 564/87; 564/89; 564/90; 564/92

(58) Field of Search .......................... 514/602, 603, 514/604, 466, 513, 524; 564/86, 87, 89, 90, 92; 549/439; 558/413; 562/12

(56) References Cited

U.S. PATENT DOCUMENTS

| | | | |
|---|---|---|---|
| 1,955,207 | 4/1934 | Stotter et al. | 167/37 |
| 2,358,365 | 9/1944 | Tullar et al. | 260/397.6 |
| 2,450,863 | 10/1948 | Altamura et al. | 260/556 |
| 2,937,202 | 5/1960 | Slagh et al. | 260/556 |
| 3,034,955 | 5/1962 | Frick et al. | 167/37 |
| 3,322,828 | 5/1967 | Muth et al. | 260/556 |
| 3,505,455 | 4/1970 | Gipstein et al. | 424/321 |
| 3,951,910 * | 4/1976 | Mark | 260/45.9 |
| 4,013,621 | 3/1977 | Knell | 260/45.9 R |
| 4,034,110 | 7/1977 | Mitrovic et al. | 424/311 |
| 4,080,379 | 3/1978 | Seng et al. | 260/556 R |
| 4,123,553 | 10/1978 | Mitrovic et al. | 424/311 |
| 4,239,699 | 12/1980 | MacKay et al. | 564/92 |
| 4,373,017 | 2/1983 | Masukawa et al. | 430/270 |
| 4,483,986 | 11/1984 | Dominianni | 544/159 |
| 4,692,466 | 9/1987 | Yoshimoto et al. | 514/604 |
| 4,851,445 | 7/1989 | Yoshimoto et al. | 514/604 |
| 4,870,107 | 9/1989 | Yoshimoto et al. | 514/604 |
| 4,918,106 | 4/1990 | Yoshimoto et al. | 514/604 |
| 5,143,937 | 9/1992 | Lang et al. | 514/603 |
| 5,280,043 | 1/1994 | Cooper et al. | 514/562 |
| 5,610,320 | 3/1997 | Yoshino et al. | 549/72 |
| 5,891,917 * | 4/1999 | Tang et al. | 514/604 |

FOREIGN PATENT DOCUMENTS

| | | |
|---|---|---|
| 859345 | 1/1961 | (CH) . |
| 1189720 | 4/1970 | (CH) . |
| 622494 | 11/1935 | (DE) . |
| 938890 | 10/1963 | (GB) . |
| 1306564 | 2/1973 | (GB) . |

OTHER PUBLICATIONS

Taniuchi et al., Chem. Abst. 82: 126077, 1975.*
Popoff, et al.; "Antimalarial Agents. 8 Ring–Substituted Bis(4–aminophenyl) Sulfones and Their Precursors"; *Journal of Medicinal Chemistry*, vol. 14, No. 12, Dec. 1971, pp. 1166–1169, XP–002083052.
De Benedetti, et al.; "Quantitative Structure–Activity Analysis in Dihydropteroate Synthase Inhibition by Sulfones. Comparison with Sulfanilamides"; *Journal of Medicinal Chemistry*, vol. 30, No. 3, Mar. 1987, pp. 459–464, XP–002083053.
Chivers, et al.; "Studies in the Chemistry of Polyhalogenobenzene Compounds. The Synthesis and Reactivity of 2,3,5,6– and 2,3,4,5—Tetrachlorobenzenesulphonyl Chlorides and Related Compounds"; *Australian Journal of Chemistry*, vol. 29, No. 7, Jul. 1976, pp. 1572–1582, XP–002083174.
Chemical Abstracts, vol. 50, No. 1, Jan. 10, 1956, Columbus, Ohio, USA; abstract No. 217g, V.O. Lukashevich: "Sulfonation of halogen–substituted benzene derivatives. Formation of anhydrides of corresponding sulphonic acids"; Column 217; XP–002083056—see abstract & DOKLADY AKAD. NAUK S.S.S.R., vol. 99, 1954, pp. 995–998.
Chemical Abstracts, vol. 74, No. 14, Apr. 5, 1971, Columbus, Ohio, USA; abstract No. 65535a, D. Simov, et al.: "Preparation of azo dyes containing a mobile chlorine atom in the benzene ring", pp 81; XP–002083055 see abstract & IZV. OTD. KHIM. NAUKI, BULG. AKAD. NAUK, vol. 3, No. 1, 1970, pp. 69–82.
V.N. Babushkin, et al.; "Influence of Substituents on the Frequency of Stretching Vibrations of Sulfur–Containing Bridging Groups in Diphenyl Systems"; *Journal of General Chemistry of the USSR*, vol. 58, No. 7, pt. 2, Jul. 1988, pp. 1457–1460, XP–002083054.

* cited by examiner

*Primary Examiner*—Peter O'Sullivan
(74) *Attorney, Agent, or Firm*—Townsend and Townsend and Crew LLP

(57) ABSTRACT

The invention provides compounds, compositions and methods relating to novel electrophilic aromatic derivatives and their use as pharmacologically active agents. The compositions find particular use as pharmacological agents in the treatment of disease states, particularly cancer, psoriasis, vascular restenosis, infections, atherosclerosis and hypercholesterolemia, or as lead compounds for the development of such agents. The compositions include compounds of the general Formula I:

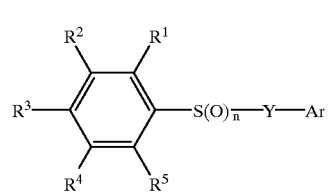

16 Claims, No Drawings

SUBSTITUTED BENZENE COMPOUNDS AS ANTIPROLIFERATIVE AND CHOLESTEROL LOWERING ACTION

INTRODUCTION

1. Field of the Invention

The field of the invention is a particular class of substituted benzene derivatives and analogs and their use as pharmacologically active agents capable of lowering plasma cholesterol levels and inhibiting abnormal cell proliferation.

2. Background

Atherosclerosis is a leading cause of death in the United States. The disease results from excess cholesterol accumulation in the arterial walls, which forms plaques that inhibit blood flow and promote clot formation, ultimately causing heart attacks, stroke and claudication. A principal source of these cholesterol deposits is the low-density lipoprotein (LDL) particles that are present in the blood. There is a direct correlation between LDL concentration and plaque formation in the arteries. LDL concentration is itself largely regulated by the supply of active LDL cell surface receptors, which bind LDL particles and translocate them from the blood into the cell's interior. Accordingly, the upregulation of LDL receptor expression provides an important therapeutic target.

Lipoprotein disorders have been previously called the hyperlipoproteinemias and defined as the elevation of a lipoprotein level above normal. The hyperlipoproteinemias result in elevations of cholesterol, triglycerides or both, and are clinically important because of their contribution to atherosclerotic diseases and pancreatitis.

Lipoproteins are spherical macromolecular complexes of lipid and protein. The lipid constituents of lipoproteins are esterified and unesterified (free) cholesterol, triglycerides, and phospholipids. Lipoproteins transport cholesterol and triglycerides from sites of absorption and synthesis to sites of utilization. Cholesteryl esters and triglycerides are nonpolar and constitute the hydrophobic core of lipoproteins in varying proportions. The lipoprotein surface coat contains the polar constituents—free cholesterol, phospholipids, and apolipoproteins—that permit these particles to be miscible in plasma.

Cholesterol is used for the synthesis of bile acids in the liver, the manufacture and repair of cell membranes, and the synthesis of steroid hormones. There are both exogenous and endogenous sources of cholesterol. The average American consumes about 450 mg of cholesterol each day and produces an additional 500 to 1,000 mg in the liver and other tissues. Another source is the 500 to 1,000 mg of biliary cholesterol that is secreted into the intestine daily; about 50 percent is reabsorbed (enterohepatic circulation). The rate-limiting enzyme in endogenous cholesterol synthesis is 3-hydroxy-3-methylglutaryl coenzyme A (HMG-CoA) reductase. Triglycerides, which are nonpolar lipids consisting of a glycerol backbone and three fatty acids of varying length and degrees of saturation, are used for storage in adipose tissue and for energy.

Lipoproteins are classified into groups based upon size, density, electrophoretic mobility, and lipid and protein composition. Very low density lipoproteins (VLDL) are large, triglyceride-rich lipoproteins that are synthesized and secreted by hepatocytes. VLDL interacts with lipoprotein lipase in capillary endothelium, and the core triglycerides are hydrolyzed to provide fatty acids to adipose and muscle tissue. About half of the catabolized VLDL particles are taken up by hepatic LDL receptors and the other half remain in plasma, becoming intermediate-density lipoprotein (IDL). IDL is enriched in cholesteryl esters relative to triglycerides and is gradually converted by hepatic triglyceride lipase to the smaller, denser, cholesterol ester-rich LDL. As IDL is converted to LDL, apolipoprotein E becomes detached, and only one apolipoprotein remains, apo B-100.

LDL normally carries about 75 percent of the circulating cholesterol. Cellular LDL uptake is mediated by a glycoprotein receptor molecule that binds to apo B-100. Approximately 70 percent of LDL is cleared by receptor uptake, and the remainder is removed by a scavenger cell pathway using nonreceptor mechanisms. The LDL receptors span the thickness of the cell's plasma membrane and are clustered in specialized regions where the cell membrane is indented to form craters called coated pits. These pits invaginate to form coated vesicles, where LDL is separated from the receptor and delivered to a lysosome so that digestive enzymes can expose the cholesteryl ester and cleave the ester bond to form free cholesterol. The receptor is recycled to the cell surface.

As free cholesterol liberated from LDL accumulates within cells, there are three important metabolic consequences. First, there is a decrease in the synthesis of HMG-CoA reductase, the enzyme that controls the rate of de novo cholesterol biosynthesis by the cell. Second, there is activation of the enzyme acyl cholesterol acyl transferase (ACAT), which esterifies free cholesterol into cholesterol ester, the cell's storage form of cholesterol. Third, accumulation of cholesterol suppresses the cell's synthesis of new LDL receptors. This feedback mechanism reduces the cell's uptake of LDL from the circulation.

Lipoproteins play a central role in atherosclerosis. This association with the most common cause of death in the developed world defines the principal clinical importance of the hyperlipoproteinemias. Individuals with an elevated cholesterol level are at higher risk for atherosclerosis. Multiple lines of evidence, including epidemiological, autopsy, animal studies and clinical trials, have established that LDL is atherosclerogenic and that the higher the LDL level, the greater the risk of atherosclerosis and its clinical manifestations. A certain degree of LDL elevation appears to be a necessary factor in the development of atherosclerosis, although the process is modified by many other factors (e.g., blood pressure, tobacco use, blood glucose level, antioxidant level, and clotting factors). Acute pancreatitis is another major clinical manifestation of dyslipoproteinemia. It is associated with chylomicronemia and elevated VLDL levels. Most patients with acute pancreatitis have triglyceride levels above 2,000 mg/dL, but a 1983 NIH consensus development conference recommended that prophylactic treatment of hypertriglyceridemia should begin when fasting levels exceed 500 mg/dL. The mechanism by which chylomicronemia and elevated VLDL levels cause pancreatitis is unclear. Pancreatic lipase may act on triglycerides in pancreatic capillaries, resulting in the formation of toxic fatty acids that cause inflammation.

Abundant evidence indicates that treatment of hyperlipoproteinemia will diminish or prevent atherosclerotic complications. In addition to a diet that maintains a normal body weight and minimizes concentrations of lipids in plasma, therapeutic agents that lower plasma concentrations of lipoproteins, either by diminishing the production of lipoproteins or by enhancing the efficiency of their removal from plasma, are clinically important.

The most promising class of drugs currently available for the treatment of hyperlipoproteinemia or hypercholesterolemia acts by inhibiting HMG-CoA reductase, the rate-limiting enzyme in endogenous cholesterol synthesis. Drugs of this class competitively inhibit the activity of the enzyme. Eventually, this inhibition leads to a decrease in the endogenous synthesis of cholesterol and by normal homeostatic mechanisms, plasma cholesterol is taken up by LDL receptors to restore the intracellular cholesterol balance.

Through both the release of precursors of LDL and receptor-mediated LDL uptake from the serum, liver cells play a critical role in maintaining serum cholesterol homeostasis. In both man and animal models, an inverse correlation appears to exist between liver LDL receptor expression levels and LDL-associated serum cholesterol levels. In general, higher hepatocyte LDL receptor numbers result in lower LDL-associated serum cholesterol levels. Cholesterol released into hepatocytes can be stored as cholesteryl esters, converted into bile acids and released into the bile duct, or it can enter into an oxycholesterol pool. It is this oxycholesterol pool that is believed to be involved in end product repression of both the genes of the LDL receptor and enzymes involved in the cholesterol synthetic pathway.

Transcription of the LDL receptor gene is known to be repressed when cells have an excess supply of cholesterol, probably in the form of oxycholesterol. A DNA sequence in the LDL receptor promoter region, known as the sterol response element (SRE), appears to confer this sterol end product repression. This element has been extensively investigated (Brown, Goldstein and Russell, U.S. Pat. Nos. 4,745,060 and 4,935,363). The SRE can be inserted into genes that normally do not respond to cholesterol, conferring sterol end product repression of the chimeric gene. The exact mechanism of the repression is not understood. Brown and Goldstein have disclosed methods for employing the SRE in a screen for drugs capable of stimulating cells to synthesize LDL receptors (U.S. Pat. No. 4,935,363). It would be most desirable if the synthesis of LDL receptors could be upregulated at the level of gene expression.

The upregulation of LDL receptor synthesis at this level offers the promise of resetting the level of serum cholesterol at a lower, and clinically more desirable, level. Presently, however, there are no cholesterol lowering drugs that are known to operate at the level of gene expression. The present invention describes methods and compounds that act to inhibit directly or indirectly the repression of the LDL receptor gene, resulting in induction of the LDL receptor on the surface of liver cells, facilitating LDL uptake, bile acid synthesis and secretion to remove cholesterol metabolites and hence the lowering of LDL-associated serum cholesterol levels.

A number of human diseases stem from processes of uncontrolled or abnormal cellular proliferation. Most prevalent among these is cancer, a generic name for a wide range of cellular malignancies characterized by unregulated growth, lack of differentiation, and the ability to invade local tissues and metastasize. These neoplastic malignancies affect, with various degrees of prevalence, every tissue and organ in the body. A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disruptors (e.g., vincristine, vinblastine, paclitaxel), DNA intercalators (e.g., doxorubicin, daunomycin, cisplatin), and hormone therapy (e.g., tamoxifen, flutamide). The ideal antineoplastic drug would kill cancer cells selectively, with a wide therapeutic index relative to its toxicity towards non-malignant cells. It would also retain its efficacy against malignant cells even after prolonged exposure to the drug. Unfortunately, none of the current chemotherapies possess an ideal profile. Most possess very narrow therapeutic indexes, and in practically every instance cancerous cells exposed to slightly sublethal concentrations of a chemotherapeutic agent will develop resistance to such an agent, and quite often cross-resistance to several other antineoplastic agents.

Psoriasis, a common chronic skin disease characterized by the presence of dry scales and plaques, is generally thought to be the result of abnormal cell proliferation. The disease results from hyperproliferation of the epidermis and incomplete differentiation of keratinocytes. Psoriasis often involves the scalp, elbows, knees, back, buttocks, nails, eyebrows, and genital regions, and may range in severity from mild to extremely debilitating, resulting in psoriatic arthritis, pustular psoriasis, and exfoliative psoriatic dermatitis. No therapeutic cure exists for psoriasis. Milder cases are often treated with topical corticosteroids, but more severe cases may be treated with antiproliferative agents, such as the antimetabolite methotrexate, the DNA synthesis inhibitor hydroxyurea, and the microtubule disrupter colchicine.

Other diseases associated with an abnormally high level of cellular proliferation include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection, where endothelial cells are involved, infectious diseases such as HIV infection and malaria, where certain immune cells and/or other infected cells are involved, and the like. Infectious and parasitic agents per se (e.g. bacteria, trypanosomes, fungi, etc) are also subject to selective proliferative control using the subject compositions and compounds.

Accordingly, it is one object of the present invention to provide compounds which directly or indirectly upregulate LDL receptor synthesis at the level of gene expression and are useful in the treatment of hypercholesterolemia or hyperlipoproteinemia.

A further object of the present invention is to provide therapeutic compositions for treating said conditions.

A further object of the invention is to provide therapeutic compositions for treating pancreatitis.

Still further objects are to provide methods for upregulating LDL receptor synthesis, for lowering serum LDL cholesterol levels, and for preventing and treating atherosclerosis.

A further object of the present invention is to provide compounds which directly or indirectly are toxic to actively dividing cells and are useful in the treatment of cancer, viral and bacterial infections, vascular restenosis, inflammatory diseases, autoimmune diseases, and psoriasis.

A further object of the present invention is to provide therapeutic compositions for treating said conditions.

Still further objects are to provide methods for killing actively proliferating cells, such as cancerous, bacterial, or epithelial cells, and treating all types of cancers, infections, inflarnmatory, and generally proliferative conditions. A further object is to provide methods for treating other medical conditions characterized by the presence of rapidly proliferating cells, such as psoriasis and other skin disorders.

Other objects, features and advantages will become apparent to those skilled in the art from the following description and claims.

SUMMARY OF THE INVENTION

The invention provides methods and compositions relating to novel substituted benzene derivatives and analogs and their use as pharmacologically active agents. The compositions find particular use as pharmacological agents in the treatment of disease states, particularly hypercholesterolemia, atherosclerosis, cancer, bacterial infections, and psoriasis, or as lead compounds for the development of such agents. The invention provides novel methods for treating pathology such as hypercholesterolemia, atherosclerosis, pancreatitis, and hyperlipoproteinemia, including administering to a patient an effective formulation of one or more of the subject compositions.

In one embodiment, the invention provides compounds of general Formula I:

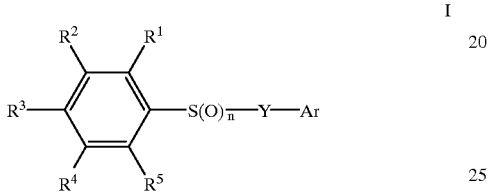

or a pharmaceutically acceptable salt thereof, wherein:

$R^1$, $R^2$, $R^4$, and $R^5$ are independently selected from hydrogen, lower alkyl, halogen, $OCF_3$, $CF_3$, $NO_2$, $CO_2H$, $CN$, $SO_2$—$N(R^6)(R^7)$, $SO_2$—$R^8$, $CO_2$—$R^8$, and $CO$—$R^8$;

$R^3$ is a leaving group, such as halogen, $NO_2$, $OCF_3$, $S(O)$—Ar, $SO_2$—$R^8$, $SO_2$—Ar, $N_3$, $N(R^6)$—$SO_2$—$CF_3$, $N(R^6)$—$SO_2$—$R^8$, $N(R^6)$—$SO_2$—Ar, $N(R^6)$—$CO$—$R^8$, $N(R^6)$—$CO$—Ar, $N[CO$—$R^8]_2$, $N(R^8)_3^+$, $N(R^8)_2(Ar)^+$, $O$—$SO_2$—Ar, $O$—$SO_2$—$R^8$, $O$—$SO_2$—$CF_3$, $O$—$CO$—$(R^8)$, $O$—$CO$—Ar, $O$—Ar, $O$—$R^8$, and $O$—$CO$—$CF_3$;

Y is a single bond, —O—, —$N(R^9)$—, —$N(R^9)$—$CH_2$—, or —$CH(R^9)$—;

and Ar is an optionally substituted aryl or heteroaryl group;

wherein $R^6$ and $R^7$ are independently chosen from hydrogen, lower alkyl, and lower heteroalkyl;

$R^8$ is selected from lower alkyl or lower heteroalkyl; and $R^9$ is selected from:
hydrogen,
substituted or unsubstituted (C1–C10)alkyl,
substituted or unsubstituted (C1–C10)alkoxy,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl-(C3–C8)cycloalkyl,
substituted or unsubstituted aryl-(C5–C7)cycloalkenyl,
substituted or unsubstituted aryloxy-(C3–C8) cycloalkyl,
substituted or unsubstituted aryl-(C1–C4)alkyl,
substituted or unsubstituted aryl-(C1–C4)alkoxy,
substituted or unsubstituted aryl-(C1–C4)heteroalkyl,
substituted or unsubstituted aryl-(C3–C6)alkenyl,
substituted or unsubstituted aryloxy-(C1–C4)alkyl,
substituted or unsubstituted aryfoxy-(C2–C4) heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4) heteroalkyl,
substituted or unsubstituted heteroaryl-(C3–C6) alkenyl,
substituted or unsubstituted heteroaryloxy-(C1–C4) alkye , and
substituted or unsubstituted heteroaryloxy-(C2–C4) heteroalkyl,
wherein, if Y is —$N(R^9)$—, then $R^9$ and Ar may be connected by a linking group E to give a substituent of the Formula

wherein E represents a bond, (C1–C4) alkylene, or (C1–C4) heteroalkylene, and the ring formed by $R^9$, E, Ar and the nitrogen atom contains no more than 8 atoms, or preferably $R^9$ and Ar may be covalently joined in a moiety that forms a 5- or 6-membered heterocyclic ring with the nitrogen atom;

with the following provisos:

At least one of the $R^1$, $R^2$, $R^4$, and $R^5$ groups is other than hydrogen or lower alkyl;

When $R^1=R^2=R^3=R^4=R^5=F$, then Y is a single bond or —$CH(R^9)$—;

When $R^1=R^2=R^3=R^4=R^5=Cl$, n=2, and Y=—NH—, then Ar is other than unsubstituted phenyl or unsubstituted p-biphenyl;

When $R^1=R^2=R^3=R^4=R^5=Br$, n=2, and Y=—NH—, then Ar is other than unsubstituted phenyl;

When $R^3$=halogen, n=2, Y=—NH— or —$N(R^9)$—, and at least one of $R^1$, $R^2$, $R^4$ and $R^5$ is also halogen, then at least one of $R^1$, $R^2$, $R^4$ and $R^5$ must be other than hydrogen;

When $R^1$=H, n=2, and Y=—NH—, then at least one of $R^2$, $R^3$, $R^4$ and $R^5$ must be a substituent other than chloro;

When $R^1=R^5$=H, n=2, and Y=—$N(R^9)$—, then at least one of $R^2$, $R^3$, and $R^4$ must be a substituent other than chloro;

When $R^1=R^5$=halogen, $R^2=R^4$=H, n=2, and Y=—$N(R^9)$—, then $R^3$ is a substituent other than chloro or bromo;

When $R^1=R^2$=halogen, $R^4=R^5$=H, n=2, and Y=—$N(R^9)$—, then $R^3$ is a substituent other than chloro or bromo;

When $R^1=R^4$=halogen, $R^2=R^5$=H, and n=2, then $R^3$ is a substituent other than chloro or bromo;

When $R^1=R^5$=halogen, $R^2=R^4$=H, and Y=—O—, then Ar is a ring system other than quinolinyl;

When $R^1$=F, $R^3=R^4$=Cl, and Y=—NH—, then Ar is a ring system other than 1,3,4-thiadiazolyl;

When $R^1=R^3$=F, $R^4$=Cl, and Y=—NH— or —O—, then Ar is a ring other than unsubstituted phenyl;

When $R^1=R^3=R^5$=Br, and Y=—NH—, then Ar is a ring other than phenyl substituted by lower-alkyl;

When $R^1=R^3=R^5Cl$, $Y=$—NH—, and $R^9=$H or methyl, then Ar is a phenyl ring substituted by 1–4 groups chosen independently from halogen, OH, OR', NH$_2$, NHR', and NR'R", wherein R' and R" are as defined below;

When $R^2=R^3=R^4=Cl$, $Y=$—NH—, and $R^9=$propargyl, then Ar is an unsubstituted ring or a ring substituted by a group other than trifluoromethyl or nitro;

When $R^1=R^3=Cl$, and $Y=$—N($R^9$)—, then $R^2$ and $R^4$ must both be other than chloro;

When $R^2=CF_3$, $R^3=Cl$, and $Y=$—N($R^9$)—, then Ar cannot be either a phenyl ring substituted by trifluoromethyl, nitro, chloro, or lower-alkyl groups, or a 2-benzothiazolyl ring;

When $R^2=CO_2H$ or $NO_2$, $R^3=Cl$, and $Y=$—N($R^9$)—, then Ar is an unsubstituted phenyl or phenyl substituted by a substituent other than $CO_2H$ or $CO_2R'$;

When $R^1=NO_2$, $R^3=Cl$, and $Y=$—NH—, then Ar is a ring system other than phenyl substituted by either Br or $NO_2$.

Substituents for the alkyl, alkoxy, alkenyl, heteroalkyl, heteroalkenyl, alkynyl, cycloalkyl, heterocycloalkyl, cycloalkenyl, and cycloalkadienyl radicals are selected independently from
—H
—OH
—O-(C1–C10)alkyl
=O
—NH$_2$
—NH-(C1–C10)alkyl
—N[(C1–C10)alkyl]$_2$
—SH
—S-(C1–C10)alkyl
—halo
—Si[(C1–C10)alkyl]$_3$ in a number ranging from zero to (2N+1), where N is the total number of carbon atoms in such radical.

Substituents for the aryl and heteroaryl groups are selected independently from
—halo
—OH
—O—R'
—O—C(O)—R'
—NH$_2$
—NHR'
—NR'R"
—SH
—SR'
—R'
—CN
—NO$_2$
—CO$_2$H
—CO$_2$—R'
—CONH$_2$
—CONH—R'
—CONR'R"
—O—C(O)—NH—R'
—O—C(O)—NR'R"
—NH—C(O)—R'
—NR"—C(O)—R'
—NH—C(O)—OR'
—NR"—C(O)—R'
—NH—C(NH$_2$)=NH
—NR'—C(NH$_2$)=NH
—NH—C(NH$_2$)=NR'
—S(O)—R'
—S(O)$_2$—R'
—S(O)$_2$—NH—R'
—S(O)$_2$—NR'R"
—N$_3$
—CH(Ph)$_2$
substituted or unsubstituted aryloxy
substituted or unsubstituted arylamino
substituted or unsubstituted heteroarylamino
substituted or unsubstituted heteroaryloxy
substituted or unsubstituted aryl-(C1–C4)alkoxy,
substituted or unsubstituted heteroaryl-(C1–C4)alkoxy,
perfluoro(C1–C4)alkoxy, and
perfluoro(C1–C4)alkyl,
in a number ranging from zero to the total number of open valences on the aromatic ring system;
and where R' and R" are independently selected from:
substituted or unsubstituted (C1–C8)alkyl,
substituted or unsubstituted (C1–C10)heteroalkyl,
substituted or unsubstituted (C2–C6)alkenyl,
substituted or unsubstituted (C2–C6)heteroalkenyl,
substituted or unsubstituted (C2–C6)alkynyl,
substituted or unsubstituted (C3–C8)cycloalkyl,
substituted or unsubstituted (C3–C8)heterocycloalkyl,
substituted or unsubstituted (C5–C6)cycloalkenyl,
substituted or unsubstituted (C5–C6)cycloalkadienyl,
substituted or unsubstituted aryl,
substituted or unsubstituted aryl-(C1–C4)alkyl,
substituted or unsubstituted aryl-(C1–C4)heteroalkyl,
substituted or unsubstituted aryl-(C2–C6)alkenyl,
substituted or unsubstituted aryloxy-(C1–C4)alkyl,
substituted or unsubstituted aryloxy-(C1–C4) heteroalkyl,
substituted or unsubstituted heteroaryl,
substituted or unsubstituted heteroaryl-(C1–C4)alkyl,
substituted or unsubstituted heteroaryl-(C1–C4) heteroalkyl,
substituted or unsubstituted heteroaryl-(C2–C6) alkenyl,
substituted or unsubstituted heteroaryloxy-(C1–C4) alkyl, and
substituted or unsubstituted heteroaryloxy-(C1–C4) heteroalkyl.

Two of the substituents on adjacent atoms of the aryl or heteroaryl ring may optionally be replaced with a substituent of the Formula —T—C(O)—(CH$_2$)$_n$—U—, wherein T and U are independently selected from N, O, and C, and n=0–2. Alternatively, two of the substituents on adjacent atoms of the aryl or heteroaryl ring may optionally be replaced with a substituent of the Formula —A—(CH2)p—B—, wherein A and B are independently selected from C, O, N, S, SO, SO$_2$, and SO$_2$NR', and p=1–3. One of the single bonds of the new ring so formed may optionally be replaced with a double bond. Alternatively, two of the substituents on adjacent atoms of the aryl or heteroaryl ring may optionally be replaced with a substituent of the Formula —(CH$_2$)$_q$—X—(CH$_2$)$_r$—, where q and r are independently selected from 1–3, and X is selected from O, N, S, SO, SO$_2$ and SO$_2$NR'. The substituent R' in SO$_2$NR' is selected from hydrogen or (C1–C6)alkyl.

In another embodiment, the invention provides for the pharmaceutical use of compounds of the general Formula I and for pharmaceutically acceptable compositions of compounds of Formula I:

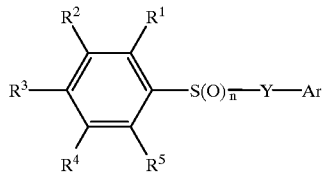

or a pharmaceutically acceptable salt thereof, wherein:
$R^1$, $R^2$, $R^4$, and $R^5$ are independently selected from hydrogen, lower alkyl, halogen, $OCF_3$, $CF_3$, $NO_2$, $CO_2H$, CN, $SO_2$—$N(R^6)(R^7)$, $SO_2$—$R^8$, $CO_2$—$R^8$, and CO—$R^8$;

$R^3$ is a leaving group, such as halogen, $NO_2$, $OCF_3$, S(O)—Ar, $SO_2$—$R^8$, $SO_2$—Ar, $N_3$, $N(R^6)$—$SO_2$—$CF_3$, $N(R^6)$—$SO_2$—$R^8$, $N(R^6)$—$SO_2$—Ar, $N(R^6)$—CO—$R^8$, $N(R^6)$—CO—Ar, $N[CO—R^8]_2$, $N(R^8)_3^+$, $N(R^8)_2(Ar)^+$, O—$SO_2$—Ar, O—$SO_2$—$R^8$, O—$SO_2$—$CF_3$, O—CO—($R^8$), O—CO—Ar, O—Ar, O—$R^8$, and O—CO—$CF_3$;

Y is a single bond, —O—, —$N(R^9)$—, —$N(R^9)$—$CH_2$—, or —$CH(R^9)$—;

and Ar is an optionally substituted aryl or heteroaryl group;

wherein $R^6$ and $R^7$ are independently chosen from hydrogen, lower alkyl, and lower heteroalkyl;

$R^8$ is selected from lower alkyl or lower heteroalkyl; and $R^9$ is selected from:
hydrogen,
substituted or unsubstituted (C1–C10)alkyl,
substituted or unsubstituted (C1–C10)alkoxy,
substituted or unsubstituted (C3–C6)alkenyl,
substituted or unsubstituted (C2–C6)heteroalkyl,
substituted or unsubstituted (C3–C6)heteroalkenyl,
substituted or unsubstituted (C3–C6)alkynyl,
substituted or unsubstituted (C3–C8)cycloalkyl,
substituted or unsubstituted (C5–C7)cycloalkenyl,
substituted or unsubstituted (C5–C7)cycloalkadienyl,
substituted or unsubstituted aryl,
substituted or unsubstituted aryloxy,
substituted or unsubstituted aryl-(C3–C8)cycloalkyl,
substituted or unsubstituted aryl-(C5–C7)cycloalkenyl,
substituted or unsubstituted aryloxy-(C3–C8) cycloalkyl,
substituted or unsubstituted aryl-(C1–C4)alkyl,
substituted or unsubstituted aryl-(C1–C4)alkoxy,
substituted or unsubstituted aryl-(C1–C4)heteroalkyl,
substituted or unsubstituted aryl-(C3–C6)alkenyl,
substituted or unsubstituted aryloxy-(C1–C4)alkyl,
substituted or unsubstituted aryloxy-(C2–C4) heteroalkyl,
substituted or unsubstituted heteroaryl,
substituted or unsubstituted heteroaryloxy,
substituted or unsubstituted heteroaryl-(C1–C4)alkyl,
substituted or unsubstituted heteroaryl-(C1–C4)alkoxy,
substituted or unsubstituted heteroaryl-(C1–C4) heteroalkyl,
substituted or unsubstituted heteroaryl-(C3–C6) alkenyl,
substituted or unsubstituted heteroaryloxy-(C1–C4) alkyl, and
substituted or unsubstituted heteroaryloxy-(C2–C4) heteroalkyl, wherein, if Y is —$N(R^9)$—, then $R^9$ and Ar may be connected by a linking group E to give a substituent of the Formula

wherein E represents a bond, (C1–C4) alkylene, or (C1–C4) heteroalkylene, and the ring formed by $R^9$, E, Ar and the nitrogen atom contains no more than 8 atoms, or preferably $R^9$ and Ar may be covalently joined in a moiety that forms a 5- or 6-membered heterocyclic ring with the nitrogen atom;

with the following provisos:
At least one of the $R^1$, $R^2$, $R^4$, and $R^5$ groups is other than hydrogen or lower alkyl;

When $R^1=R^2=R^3=R^4=R^5=F$, then Y is a single bond or —$CH(R^9)$—;

When $R^1=R^2=R^3=R^4=R^5=Cl$, n=2, and Y=—NH—, then Ar is other than unsubstituted phenyl or unsubstituted p-biphenyl;

When $R^1=R^2=R^3=R^4=R^5=Br$, n=2, and Y=—NH—, then Ar is other than unsubstituted phenyl;

When $R^3$=halogen, n=2, Y=—NH— or —$N(R^9)$—, and at least one of $R^1$, $R^2$, $R^4$ and $R^5$ is also halogen, then at least one of $R^1$, $R^2$, $R^4$ and $R^5$ must be other than hydrogen;

When $R^1$=H, n=2, and Y=—NH—, then at least one of $R^2$, $R^3$, $R^4$ and $R^5$ must be other than chloro;

When $R^1=R^5$=H, n=2, and Y=—$N(R^9)$—, then at least one of $R^2$, $R^3$, and $R^4$ must be a substituent other than chloro;

When $R^1=R^3=R^5$=Cl, Y=—NH—, and $R^9$=H or methyl, then Ar is a phenyl ring substituted by 1–4 groups chosen independently from halogen, OH, OR', $NH_2$, NHR', and NR'R", wherein R' and R" are as defined above;

When $R^1=R^3$=Cl and Y=—$N(R^9)$—, then $R^2$ and $R^4$ must both be other than chloro; and When $R^2=CF_3$, $R^3$=Cl, and Y=—$N(R^9)$—, then Ar cannot be either a phenyl ring substituted by trifluoromethyl, nitro, chloro, or lower-alkyl groups, or a 2-benzothiazolyl ring.

In yet another embodiment, the present invention provides novel methods for the use of the subject pharmaceutical compositions for treating pathology such as cancer, bacterial infections, psoriasis, hypercholesterolemia, atherosclerosis, pancreatitis, and hyperlipoproteinemia, including administering to a patient an effective formulation of one or more of the subject compositions.

DETAILED DESCRIPTION OF PARTICULAR EMBODIMENTS OF THE INVENTION

The term "alkyl" by itself or as part of another substituent means, unless otherwise stated, a straight or branched chain hydrocarbon radical, including di- and multi-radicals, having the number of carbon atoms designated (i.e. C1–C10 means one to ten carbons) and includes straight or branched chain groups such as methyl, ethyl, n-propyl, isopropyl, n-butyl, t-butyl, isobutyl, sec-butyl, homologs and isomers of n-pentyl, n-hexyl, 2-methylpentyl, 1,5-dimethylhexyl, 1-methyl-4-isopropylhexyl and the like. The term "alkylene" by itself or as part of another substituent means a divalent radical derived from an alkane, as exemplified by —$CH_2CH_2CH_2CH_2$—. A "lower alkyl" is a shorter chain alkyl, generally having six or fewer carbon atoms.

The term "heteroalkyl" by itself or in combination with another term means, unless otherwise stated, a stable straight or branched chain radical consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. The heteroatom(s) may be placed at any position of the heteroalkyl group, including between the rest of the heteroalkyl group and the fragment to which it is attached, as well as attached to the most distal carbon atom in the heteroalkyl group. Examples include —O—$CH_2$—$CH_2$—$CH_3$, —$CH_2$—$CH_2$—O—$CH_3$, —$CH_2$—$CH_2$—$CH_2$—OH, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —O—$CH_2$—$CH_2$—$CH_2$—NH—$CH_3$, and —$CH_2$—$CH_2$—$S(O)_2$—$CH_3$. Up to two heteroatoms may be consecutive, such as, for example, —$CH_2$—NH—$OCH_3$. The term "heteroalkylene" by itself or as part of another substituent means a divalent radical derived from heteroalkyl, as exemplified by —$CH_2$—$CH_2$—S—$CH_2$—$CH_2$— and —$CH_2$—S—$CH_2$—$CH_2$—NH—.

The terms "cycloalkyl" and "heterocycloalkyl", by themselves or in combination with other terms represent, unless otherwise stated, cyclic versions of "alkyl" and "heteroalkyl", respectively. Examples of cycloalkyl include cyclopentyl, cyclohexyl, cycloheptyl, and the like. Examples of heterocycloalkyl include 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "alkenyl" employed alone or in combination with other terms means, unless otherwise stated, a stable straight chain or branched monounsaturated or diunsaturated hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A divalent radical derived from an alkene is exemplified by —CH=CH—$CH_2$—.

The term "heteroalkenyl" by itself or in combination with another term means, unless otherwise stated, a stable straight or branched chain monounsaturated or diunsaturated hydrocarbon radical consisting of the stated number of carbon atoms and one or two heteroatoms selected from the group consisting of O, N, and S, and wherein the nitrogen and sulfiir atoms may optionally be oxidized and the nitrogen heteroatom may optionally be quartemized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

The term "alkynyl" employed alone or in combination with other terms means, unless otherwise stated, a stable straight chain or branched hydrocarbon group having the stated number of carbon atoms, and containing one or two carbon-carbon triple bonds, such as ethynyl, 1- and 3-propynyl, 4-but-1-ynyl, and the higher homologs and isomers.

The term "alkoxy" employed alone or in combination with other terms means, unless otherwise stated, an alkyl group, as defined above, connected to the rest of the molecule via an oxygen atom, such as, for example, methoxy, ethoxy. 1-propoxy, 2-propoxy and the higher homologs and isomers.

The terms "halo" or "halogen" by themselves or as part of another substituent mean, unless otherwise stated, a fluorine, chlorine, bromine, or iodine atom.

The term "aryl" employed alone or in combination with other terms means, unless otherwise stated, a phenyl, 1-naphthyl, or 2-naphthyl group. The maximal number of substituents allowed on each one of these ring systems is five, seven, and seven, respectively. Substituents are selected from the group of acceptable substituents listed above.

The term "heteroaryl" by itself or as part of another substituent means, unless otherwise stated, an unsubstituted or substituted, stable, mono- or bicyclic heterocyclic aromatic ring system which consists of from four to ten carbon atoms and from one to four heteroatoms selected from the group consisting of N, O, and S, and wherein the nitrogen and sulfur atoms may optionally be oxidized, and the nitrogen atom(s) may optionally be quaternized. The heterocyclic system may be attached, unless otherwise stated, at any heteroatom or carbon atom which affords a chemically stable structure. The heterocyclic system may be substituted or unsubstituted with one to four substituents independently selected from the list of acceptable aromatic substituents listed above. Examples of such heterocycles include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "lower" used alone or in combination Awith another term indicates that a radical or substituent group contains a total number of heavy atoms (carbon, oxygen, nitrogen, etc) between one and ten.

A "leaving group" as used herein is a substituent on an aromatic ring that can be displaced by a heteroatom nucleophile in an aromatic substitution or "$S_NAr$" reaction, particularly by a sulfhydryl group under physiological conditions, i.e. within the range of intracellular pH, ionic strength and temperature tolerances. Reactions of the $S_NAr$ type proceed in solution through a σ-complex (Meisenheimer complex) which may be an intermediate or a transition state; see, *Advanced Organic Chemistry*, by Jerry March, 2nd Edition, McGraw-Hill, New York: 1997, pages 594–595, and references in footnote 2 of Chapter 13. A wide variety of such leaving groups find use in the subject invention. Exemplary suitable leaving groups include: fluoro, chloro, bromo, iodo, nitro, trifluoromethoxy, Ph—S(O)—, azido, $CF_3SO_2NH$—, $PhSO_2NH$—, trimethylammonium, $PhOSO_2$—, and trifluoroacetate. Preferred leaving groups are at least as thiolate reactive as the para-fluorine substituent of the corresponding 2,3,4-trifluorobenezene moiety containing compound of the invention. Thiolate nucleophile $S_NAr$ reactivity is readily determined empirically with the assays described below or as a calculated free energy barrier; see, e.g. Zheng and Omstein (*J. Am. Chem. Soc.*, 1997, 119, 648–655). Briefly, ab initio quantum mechanical calculations including gas phase geometry optimization in the reaction intermediates and complexes are performed, e.g. at the HF/6-31+G** level of theory using GAUSSIAN 94 (Gausssian Inc., Pittburg Pa.). The solvation free energy is then calculated from the ab initio results using a solvent-effect modeling program (e.g. PS-GVB), and the overall free energy for the $S_N Ar$ reaction is obtained by adding the gas phase and solution free energy profiles.

Pharmaceutically acceptable salts of the compounds of Formula I include salts of these compounds with relatively nontoxic acids or bases, depending on the particular substituents found on specific compounds of Formula I. When compounds of Formula I contain relatively acidic functionalities, base addition salts can be obtained by contacting the neutral form of compound I with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of Formula I contain relatively basic functionalities, acid addition salts can be obtained by contacting the neutral form of compound I with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like gluconic or galactunoric acids and the like (see, for example, Berge, S. M., et al, "Pharmaceutical Salts", *Journal of pharmaceutical Science*, 1977, 66, 1–19). Certain specific compounds of Formula I contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention.

Certain compounds of the present invention possess asymmetric carbon atoms (optical centers); the racemates, diastereomers, and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$) or carbon-14 ($^{14}C$). All isotopic variations of the compounds of the present invention, whether radioactive or not, are intended to be encompassed within the scope of the present invention.

Illustrative examples of compounds and pharmaceutical compositions of the subject pharmaceutical methods include:

4-Fluoro-1-[(4-methoxyphenyl)aminosulfonyl]-3-nitrobezene;

4-Fluoro-1-[(3-hydroxy-4-methoxyphenyl)aminosulfonyl]-3-nitrobenzene;

4-Fluoro-1-[(3-fluoro-4-methoxyphenyl)aminosulfonyl]-3-nitrobenzene;

1-Bromo-3,4,5,6-tetrafluoro-2-[(3-hydroxy-4-methoxyphenyl)aminosulfonyl]benzene;

1-Bromo-3,4,5,6-tetrafluoro-2-[(4-methoxyphenyl)aminosulfonyl)]benzene;

1-Bromo-2,4,5,6-tetrafluoro-3-[(4-methoxyphenyl)aminosulfonyl)]benzene;

1-Bromo-2,3,5,6-tetrafluoro-4-[(4-methoxyphenyl)aminosulfonyl]benzene;

1-Chloro-2,3,5,6-tetrafluoro-4-[(4-methoxyphenyl)aminosulfonyl]benzene;

1,3-Dichloro-2,4,6-trifluoro-5-[(4-methoxyphenyl)aminosulfonyl]benzene;

1,3-Dichloro-2,4,6-trifluoro-5-[(3-hydroxy-4-methoxyphenyl)aminosulfonyl]benzene;

1-Bromo-4,5,6-trifluoro-2-[(4-methoxyphenyl)aminosulfonyl]benzene;

1-Bromo-4,5,6-trifluoro-3-[(3-hydroxy-4-methoxyphenyl)aminosulfonyl]benzene;

1-Bromo-4,5,6-trifluoro-2-[(3-hydroxy-4-methoxyphenyl)aminosulfonyl]benzene;

1-Bromo-3,4,5-trifluoro-2-[(3-hydroxy-4-methoxyphenyl)aminosulfonyl]benzene;

1-Bromo-3,4,5-trifluoro-2-[(3-fluoro-4-methoxyphenyl)aminosulfonyl]benzene;

2,3,4-Trifluoro-1-[(4-methoxyphenyl)aminosulfonyl]benzene;

1-Bromo-3,4,5-trifluoro-2-[(4-methoxyphenyl)aminosulfonyl]benzene;

2,3,4-Trifluoro-1-[(3-fluoro-4-methoxyphenyl)aminosulfonyl]benzene;

1-[(3-Chloro-4-methoxyphenyl)aminosulfonyl]-2,3,4-trifluorobenzene;

2,3,4-Trifluoro-1-[(3-hydroxy-4-methoxyphenyl)aminosulfonyl]benzene;

3,4,6-Trifluoro-1-[(4-methoxyphenyl)aminosulfonyl]benzene;

2,3,4,6-Tetrafluoro-1-[(4-methoxyphenyl)aminosulfonyl]benzene;

2,3,4,5-Tetrafluoro-1-[(4-methoxyphenyl)aminosulfonyl]benzene;

2,3,4,5-Tetrafluoro-1-[(3-hydroxy-4-methoxyphenyl)aminosulfonyl]benzene;

2,3,4,5-Tetrafluoro-1-[(3-fluoro-4-methoxyphenyl)aminosulfonyl]benzene;

3,4,5-Trifluoro-1-[(4-methoxyphenyl)aminosulfonyl]benzene;

3,4,5-Trifluoro-1-[(3-hydroxy-4-methoxyphenyl)aminosulfonyl]benzene;

3,4,5-Trifluoro-1-[(3-fluoro-4-methoxyphenyl)aminosulfonyl]benzene;

1-Bromo-3,4,5,6-tetrafluoro-2-[(3-fluoro-4-methoxyphenyl)aminosulfonyl]benzene;

1-Bromo-2,4,5,6-tetrafluoro-3-[(3-hydroxy-4-methoxyphenyl)aminosulfonyl]benzene;

1-Bromo-2,3,5,6-tetrafluoro-4-[(3-hydroxy-4-methoxyphenyl)aminosulfonyl]benzene;

1-Bromo-2,4,5,6-tetrafluoro-3-[(3-fluoro-4-methoxyphenyl)aminosulfonyl]benzene;
1-Bromo-2,3,5,6-tetrafluoro-4-[(3-fluoro-4-methoxyphenyl)aminosulfonyl]benzene;
1-Chloro-2,3,5,6-tetrafluoro-4-[(3-hydroxy-4-methoxyphenyl)aminosulfonyl]benzene;
1-Chloro-2,3,5,6-tetrafluoro-4-[(3-fluoro-4-methoxyphenyl)aminosulfonyl]benzene;
1,3-Dichloro-2,4,6-trifluoro-5-[(3-fluoro-4-methoxyphenyl)aminosulfonyl]benzene;
1-Bromo-4,5,6-trifluoro-3-[(3-fluoro-4-methoxyphenyl)aminosulfonyl]benzene;
4-Fluoro-1-[(4-methoxyphenyl)methylsulfonyl]-3-nitrobenzene;
2-Fluoro-5-[(4-methoxyphenyl)aminosulfonyl]benzonitrile;
2-Fluoro-5-[(3-fluoro-4-methoxyphenyl)aminosulfonyl]benzonitrile;
2-Fluoro-5-[(3-hydroxy-4-methoxyphenyl)aminosulfonyl]benzonitrile;
4,5-Difluoro-1-[(4-methoxyphenyl)aminosulfonyl]-3-nitrobenzene;
4,5-Difluoro-1-[(3-fluoro-4-methoxyphenyl)aminosulfonyl]-3-nitrobenzene;
4,5-Difluoro-1-[(3-hydroxy-4-methoxyphenyl)aminosulfonyl]-3-nitrobenzene;
4-Trifluoromethylsulfonamido-1-[(4-methoxyphenyl)aminosulfonyl]-3-nitrobenzene;
4-Trifluoromethylsulfonamido-1-[(3-fluoro-4-methoxyphenyl)aminosulfonyl]-3-nitrobenzene;
4-Trifluoromethylsulfonamido-1-[(3-hydroxy-4-methoxyphenyl)aminosulfonyl]-3-nitrobenzene;
4-(Diacetylamino)-2,3-difluoro-1-[(3-fluoro-4-methoxyphenyl)aminosulfonyl]-5-nitrobenzene;
2,3,4-Trifluoro-5-[(4-methoxyphenyl)aminosulfonyl]benzoic acid, ethyl ester;
2,3,4-Trifluoro-5-[(3-fluoro-4-methoxyphenyl)aminosulfonyl]benzoic acid, ethyl ester;
2,3,4-Trifluoro-5-[(3-hydroxy-4-methoxyphenyl)aminosulfonyl]benzoic acid, ethyl ester;
2,4,5,6-Tetrafluoro-3-[(4-methoxyphenyl)aminosulfonyl]benzoic acid, ethyl ester;
2,4,5,6-Tetrafluoro-3-[(3-fluoro-4-methoxyphenyl)aminosulfonyl]benzoic acid, ethyl ester;
2,4,5,6-Tetrafluoro-3-[(3-hydroxy-4-methoxyphenyl)aminosulfonyl]benzoic acid, ethyl ester;
1-Chloro-4-[(4-methoxyphenyl)aminosulfonyl]-2-nitrobenzene;
1-Chloro-4-[(3-fluoro-4-methoxyphenyl)aminosulfonyl]-2-nitrobenzene;
1-Chloro-4-[(3-hydroxy-4-methoxyphenyl)aminosulfonyl]-2-nitrobenzene;
4-Fluoro-1-[(3-hydroxy-4-methoxyphenyl)methylsulfonyl]-3-nitrobenzene;
4-Fluoro-1-[(4-methoxyphenyl)sulfonyl]-3-nitrobenzene;
4-Fluoro-1-[(3-hydroxy-4-methoxyphenyl)sulfonyl]-3-nitrobenzene;
1-Bromo-3,4,5,6-tetrafluoro-2-[(3-hydroxy-4-methoxyphenyl)methylsulfonyl]benzene;
1-Bromo-2,3,5,6-tetrafluoro-4-[(3-fluoro-4-methoxyphenyl)sulfonyl]benzene;
1-Bromo-2,4,5,6-tetrafluoro-3-[(4-methoxyphenyl)sulphenyl]benzene;
1,3-Dichloro-2,4,6-trifluoro-5-[(3-fluoro-4-methoxyphenyl)methylsulfonyl]benzene;
2,3,4,5-Tetrafluoro-1-[(4-methoxyphenyl)sulfonyl]benzene;
2,3,4,6-Tetrafluoro-1-[(3-hydroxy-4-methoxyphenyl)methylsulfonyl]benzene;
2-Fluoro-5-[(4-methoxyphenyl)sulfonyl]benzonitrile;
2-Fluoro-5-[(3,4-dimethoxyphenyl)methylsulfonyl]benzonitrile;
2,3,4-Trifluoro-5-[(4-dimethylaminophenyl)sulfonyl]benzoic acid, ethyl ester;
2,4,5,6-Tetrafluoro-3-[(4-dimethylaminophenyl)sulfenyl]benzoic acid, ethyl ester;
1-Chloro-4-[(4-methoxyphenyl)methylsulfonyl]-2-nitrobenzene;
1-Chloro-4-[(4-dimethylaminophenyl)sulfonyl]-2-nitrobenzene;
2-Chloro-5-[(4-methoxyphenyl)aminosulfonyl]benzonitrile;
2-Chloro-5-[(3-fluoro-4-methoxyphenyl)aminosulfonyl]benzonitrile;
2-Chloro-5-[(3-hydroxy-4-methoxyphenyl)aminosulfonyl]benzonitrile;
4-Fluoro-1-[(3,4-dimethoxyphenyl)aminosulfonyl]-3-nitrobenzene;
4-Fluoro-1-[(4-dimethylaminophenyl)aminosulfonyl]-3-nitrobenzene;
4,5-Difluoro-1-[(3,4-dimethoxyphenyl)aminosulfonyl]-3-nitrobenzene; and
4,5-Difluoro-1-[(4-dimethylaminophenyl)aminosulfonyl]-3-nitrobenzene;

Compounds of general Formula I, or a pharmaceutically acceptable salt thereof, are preferred in which:

$R^1$, $R^2$, $R^4$, and $R^5$ are independently selected from hydrogen, F, Cl, Br, $OCF_3$, $CF_3$, $SO_2$-(lower-alkyl), $NO_2$, CN, and $SO_2$—$N(R^6)(R^7)$;

$R^3$ is halogen or $OCF_3$;

n=2;

Y is a single bond, —$N(R^9)$—, or —$CH(R^9)$—;

Ar is an optionally substituted aryl or heteroaryl group;

and $R^6$, $R^7$ and $R^9$ are independently chosen from hydrogen, lower alkyl, and lower heteroalkyl.

Also preferred are compounds of Formula I in which there is no linking group E between $R^9$ and Ar.

Most preferred are compounds of Formula I in which:

$R^1$, $R^2$, $R^4$, and $R^5$ are independently selected from hydrogen, F, Cl, Br, $OCF_3$, $CF_3$, $NO_2$, and CN;

$R^3$ is halogen or $OCF_3$;

Y is —NH—;

n=2;

Ar is an optionally substituted aryl group;

$R^6$ and $R^7$ are independently selected from lower-alkyl;

$R^9$ is hydrogen;

and there is no linking group E between $R^9$ and Ar.

Preferred compounds and compositions of this embodiment of the invention have specific pharmacological properties. Examples of most preferred compounds and compositions of this embodiment of the invention include:

4-Fluoro-1-[(4-methoxyphenyl)aminosulfonyl]-3-nitrobenzene;
4-Fluoro-1-[(3-hydroxy-4-methoxyphenyl)aminosulfonyl]-3-nitrobenzene;
4-Fluoro-1-[(3-fluoro-4-methoxyphenyl)aminosulfonyl]-3-nitrobenzene;
4-Fluoro-1-[(3,4-dimethoxyphenyl)aminosulfonyl]-3-nitrobenzene; 2 5 4-Fluoro-1-[(4-aminophenyl)aminosulfonyl]-3-nitrobenzene;
2-Fluoro-5-[(4-methoxyphenyl)aminosulfonyl]benzonitrile;
2-Fluoro-5-[(3-fluoro-4-methoxyphenyl)aminosulfonyl]benzonitrile;
2-Fluoro-5-[(3-hydroxy-4-methoxyphenyl)aminosulfonyl]benzonitrile;
2-Fluoro-5-[(3,4-dimethoxyphenyl)aminosulfonyl]benzonitrile;
5-[(4-Dimethylaminophenyl)aminosulfonyl]-2-fluorobenzonitrile;
4,5-Difluoro-1-[(4-methoxyphenyl)aminosulfonyl]-3-nitrobenzene;
4,5-Difluoro-1-[(3-fluoro-4-methoxyphenyl)aminosulfonyl]-3-nitrobenzene;
4,5-Difluoro-1-[(3-hydroxy-4-methoxyphenyl)aminosulfonyl]-3-nitrobenzene;
4,5-Difluoro-1-[(3,4-dimethoxyphenyl)aminosulfonyl]-3-nitrobenzene;
4,5-Difluoro-1-[(4-aminophenyl)aminosulfonyl]-3-nitrobenzene;
2,3,4-Trifluoro-5-[(4-methoxyphenyl)aminosulfonyl]benzoic acid, ethyl ester;
2,3,4-Trifluoro-5-[(3-fluoro-4-methoxyphenyl)aminosulfonyl]benzoic acid, ethyl ester;
2,3,4-Trifluoro-5-[(3-hydroxy-4-methoxyphenyl)aminosulfonyl]benzoic acid, ethyl ester;
2,3,4-Trifluoro-5-[(3,4-dimethoxyphenyl)aminosulfonyl]benzoic acid, ethyl ester;
2,3,4-Trifluoro-5-[(4-dimethylaminophenyl)aminosulfonyl]benzoic acid, ethyl ester;
2,4,5,6-Tetrafluoro-3-[(4-methoxyphenyl)aminosulfonyl]benzoic acid, ethyl ester;
2,4,5,6-Tetrafluoro-3-[(3-fluoro-4-methoxyphenyl)aminosulfonyl]benzoic acid, ethyl ester;
2,4,5,6-Tetrafluoro-3-[(3-hydroxy-4-methoxyphenyl)aminosulfonyl]benzoic acid, ethyl ester;
2,4,5,6-Tetrafluoro-3-[(3,4-dimethoxyphenyl)aminosulfonyl]benzoic acid, ethyl ester;
2,4,5,6-Tetrafluoro-3-[(4-dimethylaminophenyl)aminosulfonyl]benzoic acid, ethyl ester;
1-Bromo-3,4,5,6-tetrafluoro-2-[(3-hydroxy-4-methoxyphenyl)aminosulfonyl]benzene;
1-Bromo-3,4,5,6-tetrafluoro-2-[(4-methoxyphenyl)aminosulfonyl)]benzene;
1-Bromo-3,4,5,6-tetrafluoro-2-[(3-fluoro-4-methoxyphenyl)aminosulfonyl]benzene;
1-Bromo-2,4,5,6-tetrafluoro-3-[(4-methoxyphenyl)aminosulfonyl)]benzene;
1-Bromo-2,4,5,6-tetrafluoro-3-[(3-hydroxy-4-methoxyphenyl)aminosulfonyl]benzene;
1-Bromo-2,4,5,6-tetrafluoro-3-[(3-fluoro-4-methoxyphenyl)aminosulfonyl]benzene;
1-Bromo-2,4,5,6-tetrafluoro-3-[(3,4-dimethoxyphenyl)aminosulfonyl]benzene;
1-Bromo-2,4,5,6-tetrafluoro-3-[(4-dimethylaminophenyl)aminosulfonyl]benzene;
1,3-Dichloro-2,4,6-trifluoro-5-[(4-methoxyphenyl)arninosulfony]benzene;
1,3-Dichloro-2,4,6-trifluoro-5-[(3-fluoro-4-methoxyphenyl)aminosulfonyl]benzene;
1,3-Dichloro-2,4,6-trifluoro-5-[(3-hydroxy-4-methoxyphenyl)aminosulfonyl]benzene;
1-Bromo-4,5,6-trifluoro-2-[(4-methoxyphenyl)aminosulfonyl]benzene;
1-Bromo-4,5,6-trifluoro-2-[(3-hydroxy-4-methoxyphenyl)aminosulfonyl]benzene;
1-Bromo-4,5,6-trifluoro-2-[(3-fluoro-4-methoxyphenyl)aminosulfonyl]benzene;
1-Bromo-4,5,6-trifluoro-2-[(3,4-dimethoxyphenyl)aminosulfonyl]benzene;
1-Bromo-2,3,4-trifluoro-5-[(3-hydroxy-4-methoxyphenyl)aminosulfonyl]benzene;
1-Bromo-2,3,4-trifluoro-5-[(3-fluoro-4-methoxyphenyl)aminosulfonyl]benzene;
1-Bromo-2,3,4-trifluoro-5-[(4-methoxyphenyl)aminosulfonyl]benzene;
1-Bromo-2,3,4-trifluoro-5-[(3,4-dimethoxyphenyl)aminosulfonyl]benzene;
1-Bromo-3,4,5-trifluoro-2-[(3-hydroxy-4-methoxyphenyl)aminosulfonyl]benzene;
1-Bromo-3,4,5-trifluoro-2-[(3-fluoro-4-methoxyphenyl)aminosulfonyl]benzene;
1-Bromo-3,4,5-trifluoro-2-[(4-methoxyphenyl)aminosulfonyl]benzene;
2,3,4,5-Tetrafluoro-1-[(4-methoxyphenyl)aminosulfonyl]benzene;
2,3,4,5-Tetrafluoro-1-[(3-hydroxy-4-methoxyphenyl)aminosulfonyl]benzene;
2,3,4,5-Tetrafluoro-1-[(3-fluoro-4-methoxyphenyl)aminosulfonyl]benzene;
2,3,4,5-Tetrafluoro-1-[(3,4-dimethoxyphenyl)aminosulfonyl]benzene;
2,3,4,5-Tetrafluoro-1-[(4-dimethylaminophenyl)aminosulfonyl]benzene;
3,4,5-Trifluoro-1-[(4-methoxyphenyl)aminosulfonyl]benzene;
3,4,5-Trifluoro-1-[(3-hydroxy-4-methoxyphenyl)aminosulfonyl]benzene;
3,4,5-Trifluoro-1-[(3-fluoro-4-methoxyphenyl)aminosulfonyl]benzene;
3,4,5-Trifluoro-1-[(3,4-dimethoxyphenyl)aminosulfonyl]benzene; or
3,4,5-Trifluoro-1-[(4-dimethylaminophenyl)aminosulfonyl]benzene.
1-Chloro-4-[(4-methoxyphenyl)aminosulfonyl]-2-nitrobenzene;
1-Chloro-4-[(3-fluoro-4-methoxyphenyl)aminosulfonyl]-2-nitrobenzene;
1-Chloro-4-[(3-hydroxy-4-methoxyphenyl)aminosulfonyl]-2-nitrobenzene;
1-Chloro-4-[(3,4-dimethoxyphenyl)aminosulfonyl]-2-nitrobenzene;
1-Chloro-4-[(4-dimethylaminophenyl)aminosulfonyl]-2-nitrobenzene;
2-Chloro-5-[(4-methoxyphenyl)aminosulfonyl]benzonitrile;

2-Chloro-5-[(3-fluoro-4-methoxyphenyl)aminosulfonyl]benzonitrile;
2-Chloro-5-[(3-hydroxy-4-methoxyphenyl)aminosulfonyl]benzonitrile.
2-Chloro-5-[(3,4-dimethoxyphenyl)aminosulfonyl]benzonitrile;
2-Chloro-5-[(4-dimethylaminophenyl)aminosulfonyl]benzonitrile;
2-Chloro-5-[(4-methoxyphenyl)aminosulfonyl]benzoic acid, ethyl ester;
2-Chloro-5-[(3-fluoro-4-methoxyphenyl)aminosulfonyl]benzoic acid, ethyl ester;
2-Chloro-5-[(3-hydroxy-4-methoxyphenyl)aminosulfonyl]benzoic acid, ethyl ester;
2-Chloro-5-[(3,4-dimethoxyphenyl)aminosulfonyl]benzoic acid, ethyl ester;
2-Chloro-5-[(4-dimethylaminophenyl)aminosulfonyl]benzoic acid, ethyl ester;
1-Chloro-2,3,5,6-tetrafluoro-4-[(4-methoxyphenyl)aminosulfonyl]benzene;
1-Chloro-2,3,5,6-tetrafluoro-4-[(3-hydroxy-4-methoxyphenyl)aminosulfonyl]benzene;
1-Chloro-2,3,5,6-tetrafluoro-4-[(3-fluoro-4-methoxyphenyl)aminosulfonyl]benzene;
1-Chloro-2,3,5,6-tetrafluoro-4-[(4-dimethylaminophenyl)aminosulfonyl]benzene;
1-Chloro-2,3,5,6-tetrafluoro-4-[(3,4-dimethoxyphenyl)aminosulfonyl]benzene;
1-Chloro-2,3,6-trifluoro-4-[(4-methoxyphenyl)aminosulfonyl]benzene;
1-Chloro-2,3,6-trifluoro-4-[(3-hydroxy-4-methoxyphenyl)aminosulfonyl]benzene;
1-Chloro-2,3,6-trifluoro-4-[(3-fluoro-4-methoxyphenyl)aminosulfonyl]benzene;
1-Chloro-2,3,6-trifluoro-4-[(4-dimethylaminophenyl)aminosulfonyl]benzene;
1-Chloro-2,3,6-trifluoro-4-[(3,4-dimethoxyphenyl)aminosulfonyl]benzene;
1-Bromo-4-[(4-methoxyphenyl)aminosulfonyl]-2-nitrobenzene;
1-Bromo-4-[(3-fluoro-4-methoxyphenyl)aminosulfonyl]-2-nitrobenzene;
1-Bromo-4-[(3-hydroxy-4-methoxyphenyl)aminosulfonyl]-2-nitrobenzene;
1-Bromo-4-[(3,4-dimethoxyphenyl)aminosulfonyl]-2-nitrobenzene;
1-Bromo-4-[(4-dimethylaminophenyl)aminosulfonyl]-2-nitrobenzene;
2-Bromo-5-[(4-methoxyphenyl)aminosulfonyl]benzonitrile;
2-Bromo-5-[(3-fluoro-4-methoxyphenyl)aminosulfonyl]benzonitrile;
2-Bromo-5-[(3-hydroxy-4-methoxyphenyl)aminosulfonyl]benzonitrile.
2-Bromo-5-[(3,4-dimethoxyphenyl)aminosulfonyl]benzonitrile;
2-Bromo-5-[(4-dimethylaminophenyl)aminosulfonyl]benzonitrile;
2-Bromo-5-[(4-methoxyphenyl)aminosulfonyl]benzoic acid, ethyl ester;
2-Bromo-5-[(3-fluoro-4-methoxyphenyl)aminosulfonyl]benzoic acid, ethyl ester;
2-Bromo-5-[(3-hydroxy-4-methoxyphenyl)aminosulfonyl]benzoic acid, ethyl ester;
2-Bromo-5-[(3,4-dimethoxy phenyl)aminosulfonyl]benzoic acid, ethyl ester;
2-Bromo-5-[(4-dimethylamxinophenyl)aminosulfonyl]benzoic acid, ethyl ester;
1-Bromo-2,3,5,6-tetrafluoro-4-[(4-methoxyphenyl)aminosulfonyl]benzene,
1-Bromo-2,3,5,6-tetrafluoro-4-[(3-hydroxy-4-methoxyphenyl)aminosulfonyl]benzene;
1-Bromo-2,3,5,6-tetrafluoro-4-[(3-fluoro-4-methoxyphenyl)aminosulfonyl]benzene;
1-Bromo-2,3,5,6-tetrafluoro-4-[(4-dimethylaminophenyl)aminosulfonyl]benzene;
1-Bromo-2,3,5,6-tetrafluoro-4-[(3,4-dimethoxyphenyl)aminosulfonyl]benzene;
1-Bromo-2,3,6-trifluoro-4-[(4-methoxyphenyl)aminosulfonyl]benzene;
1-Bromo-2,3,6-trifluoro-4-[(3-hydroxy-4-methoxyphenyl)aminosulfonyl]benzene;
1-Bromo-2,3,6-trifluoro-4-[(3-fluoro-4-methoxyphenyl)aminosulfonyl]benzene;
1-Bromo-2,3,6-trifluoro-4-[(4-dimethylaminophenyl)aminosulfonyl]benzene;
1-Bromo-2,3,6-trifluoro-4-[(3,4-dimethoxyphenyl)aminosulfonyl]benzene;
4-Trifluoromethoxy-1-[(4-methoxyphenyl)aminosulfonyl]-3-nitrobenzene;
4-Trifluoromethoxy-1-[(3-fluoro-4-methoxyphenyl)aminosulfonyl]-3-nitrobenzene;
4-Trifluoromethoxy-1-[(3-hydroxy-4-methoxyphenyl)aminosulfonyl]-3-nitrobenzene;
4-Trifluoromethoxy-1-[(3,4-dimethoxyphenyl)aminosulfonyl]-3-nitrobenzene;
4-Trifluoromethoxy-1-[(4-dimethylaminophenyl)aminosulfonyl ]-3-nitrobenzene;
2-Trifluoromethoxy-5-[(4-methoxyphenyl)aminosulfonyl]benzonitrile;
2-Trifluoromethoxy-5-[(3-fluoro-4-methoxyphenyl)aminosulfonyl]benzonitrile;
2-Trifluoromethoxy-5-[(3-hydroxy-4-methoxyphenyl)aminosulfonyl]benzonitrile.
2-Trifluoromethoxy-5-[(3,4-dimethoxyphenyl)aminosulfonyl]benzonitrile;
2-Trifluoromethoxy-5-[(4-dimethylaminophenyl)aminosulfonyl]benzonitrile;
2-Trifluoromethoxy-5-[(4-methoxyphenyl)aminosulfonyl]benzoic acid, ethyl ester;
2-Trifluoromethoxy-5-[(3-fluoro-4-methoxyphenyl)aminosulfonyl]benzoic acid, ethyl ester;
2-Trifluoromethoxy-5-[(3-hydroxy-4-methoxyphenyl)aminosulfonyl]benzoic acid, ethyl ester;
2-Trifluoromethoxy-5-[(3,4-dimethoxyphenyl)aminosulfonyl]benzoic acid, ethyl ester;
2,3,5,6-Tetrafluoro-1-trifluoromethoxy-4-[(4-methoxyphenyl)aminosulfonyl]benzene;
2,3,5,6-Tetrafluoro-1-trifluoromethoxy-4-[(3-hydroxy-4-methoxyphenyl)aminosulfonyl]benzene;
2,3,5,6-Tetrafluoro-1-trifluoromethoxy-4-[(3-fluoro-4-methoxyphenyl)aminosulfonyl]benzene;
2,3,5,6-Tetrafluoro-1-trifluoromethoxy-4-[(4-dimethylaminophenyl)aminosulfonyl]benzene;

2,3,5,6-Tetrafluoro-1-trifluoromethoxy-4-[(3,4-dimethoxyphenyl)aminosulfonyl]benzene;

2,3,6-Trifluoro-1-trifluoromethoxy-4-[(4-methoxyphenyl)aminosulfonyl]benzene;

2,3,6-Trifluoro-1-trifluoromethoxy-4-[(3-hydroxy-4-methoxyphenyl)aminosulfonyl]benzene;

2,3,6-Trifluoro-1-trifluoromethoxy-4-[(3-fluoro-4-methoxyphenyl)aminosulfonyl]benzene;

2,3,6-Trifluoro-1-trifluoromethoxy-4-[(4-dimethylaminophenyl)aminosulfonyl]benzene; or 2,3,6-Trifluoro-1-trifluoromethoxy-4-[(3,4-dimethoxyphenyl)aminosulfonyl]benzene.

Synthesis

The invention provides methods of making the subject compounds and compositions. In one general embodiment, the methods involve combining an appropriate sulfonyl chloride (iii) with an appropriate aniline (iv), as outlined in Scheme 1, to yield a sulfonamide (v). The necessary sulfonyl chlorides (iii) can be prepared by sulfonation of the appropriately substituted aromatic compounds (i) with fuming sulfuric acid, followed by treatment with a chlorinating agent, such as PCl$_5$, POCl$_3$ and the like, to afford the corresponding sulfonyl chlorides (iii), (Scheme 1). When the sulfonamides contain certain groups, such as chloro or bromo, these groups can be catalytically reduced to produce yet other analogous sulfonamides (vi).

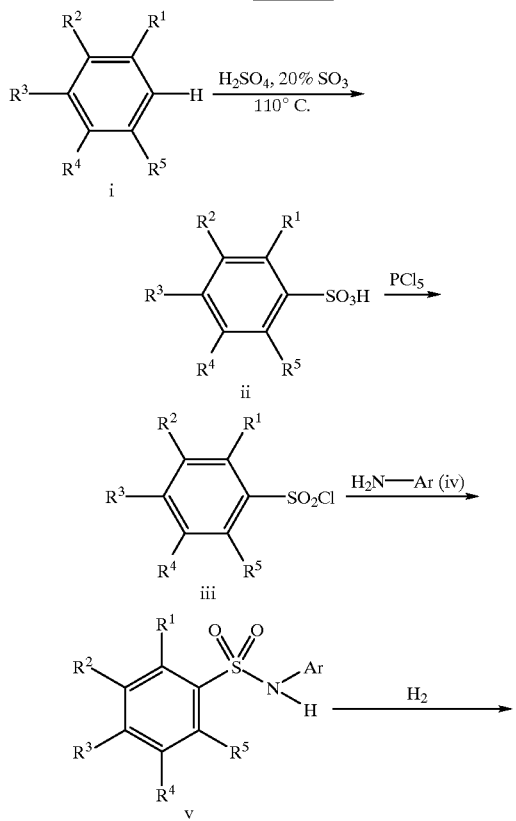

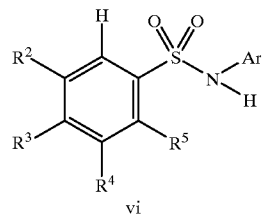

(when R$^1$ = Cl or Br)

An alternative way of preparing the desired sulfonyl chlorides (iii) is by heating the starting aromatic compounds (i) with chlorosulfonic acid as shown in Scheme 2.

Scheme 2

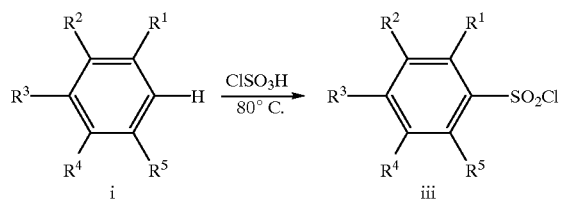

Alternatively, the desired sulfonyl chlorides (iii) are prepared from their corresponding anilines (vii) by dissolving the aniline in an acidic aqueous solution, such as HCl and the like, followed by addition of an aqueous solution of sodium nitrite at a temperature below ambient temperature, typically between −20 and +5° C. The resulting mixture, containing the desired diazonium salt, is then added to a saturated solution of sulfur dioxide in glacial acetic acid containing cuprous chloride, at a temperature between −10 and +10° C., to yield the corresponding sulfonyl chloride (iii) (see Scheme 3).

Scheme 3

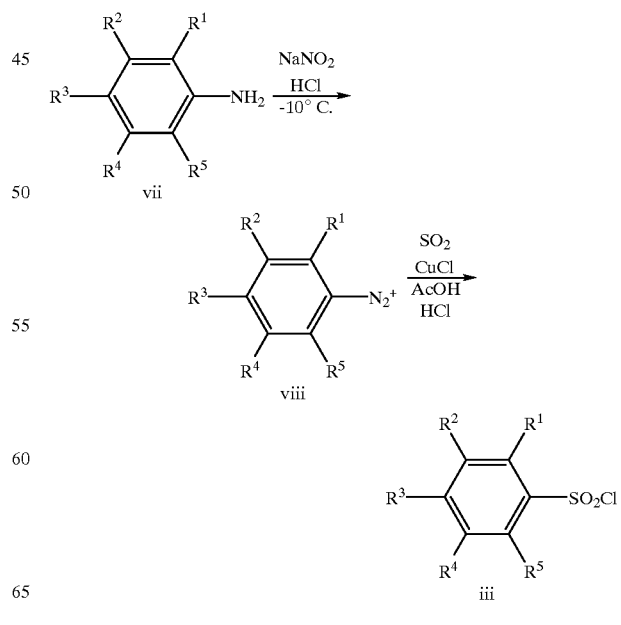

The desired sulfonyl chlorides (iii) can also be prepared by oxidation of the respective thiophenols (ix) with chlorine and hydrogen peroxide in acetic acid as shown in Scheme 4.

Scheme 4

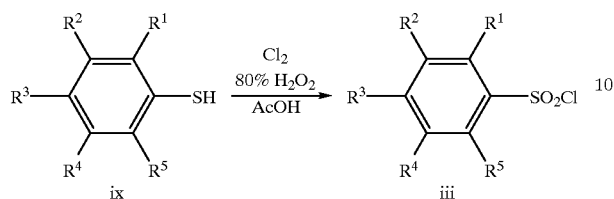

The sulphinamides described in this patent can be synthesized by reaction of the desired sulfinyl chlorides (xiii) with the appropriate amine (iv), as shown in Scheme 5. The necessary sulfinyl chlorides (xiii) are prepared by metal—halogen exchange reaction on the appropriate aryl bromides (x), chlorides or iodides, with an alkyllithium reagent such as butyl-lithium, or with magnesium metal, followed by treatment of the resulting aryl organometallic compounds (xi) with sulfur dioxide affords the lithium sulfinates (xii) that can be further reacted with thionyl chloride to afford the desired sulfinyl chlorides (xiii).

Scheme 5

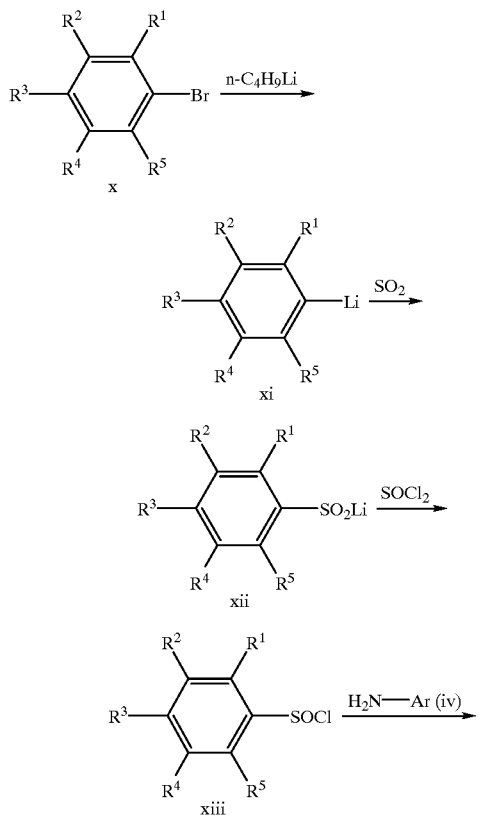

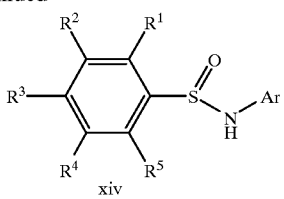

The sulfoxides (xviii) and sulfones (xix) described in this patent can be prepared by reaction of the desired substituted thiophenols (xv) with the derivatized benzylic halides (xvi) to yield the corresponding sulfides (xvii), which can be oxidized to the corresponding sulfoxides (xviii) or sulfones (xix) according to Scheme 6. The necessary thiophenols (xv) can be prepared from the starting substituted anilines (vii) by diazotization, followed by treatment with sodium sulfide (Scheme 6).

Alternatively, the thiophenols (xv) can be prepared by treatment of the diazonium salts (viii) with potassium ethyl xanthate, followed by saponification of the resulting xanthates (xx), as shown in Scheme 7. Other alternate methods for the synthesis of the desired substituted thiophenols (xv) are described in the chemical literature and are well known to individuals versed in the art of organic synthesis.

Scheme 6

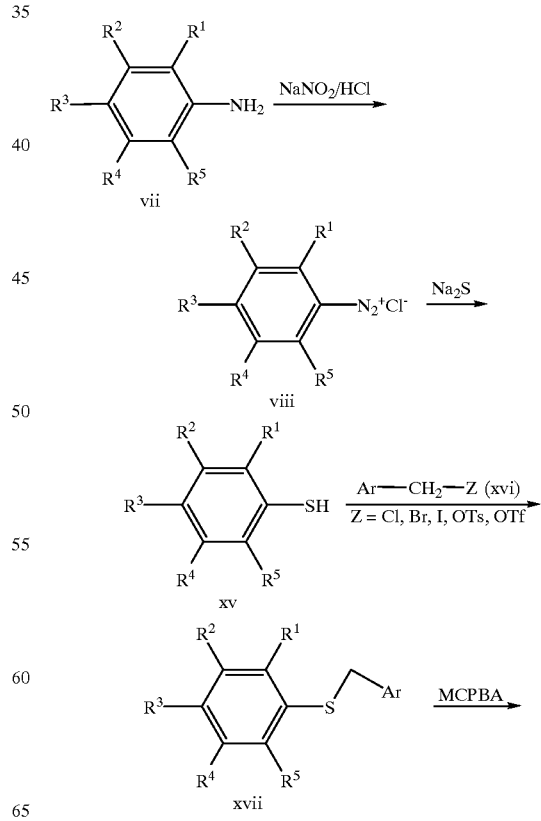

-continued

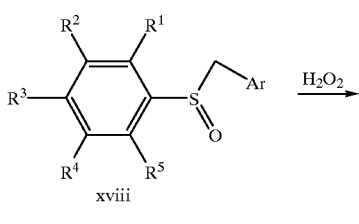

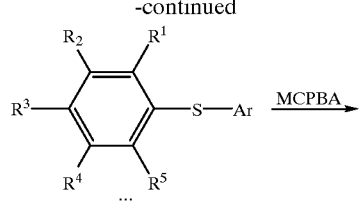

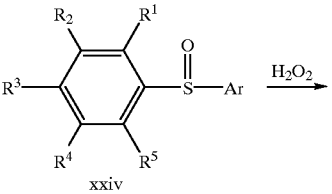

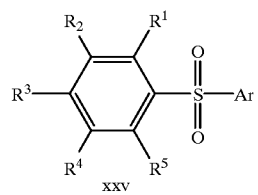

Scheme 7

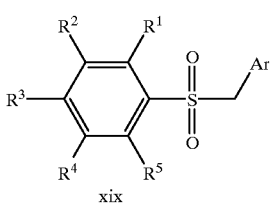

Sulfoxides (xxiv) and sulfones (xxv) wherein both aromatic rings are directly attached to S can be prepared as shown in Scheme 8. The reaction of fluorobenzene derivatives (xxi) with substituted thiophenols (xxii) provides the diaryl sulfides (xxiii). Oxidation of these sulfides provides the desired sulfoxides (xxiv) or sulfones (xxv).

Scheme 8

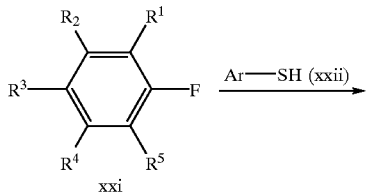

In cases where the desired compounds of Formula I contain one or more bromine, chlorine, or iodide atoms, these can be hydrogenated in the presence of a catalyst, such as palladium on carbon, to give the corresponding dehalogenated compounds. This process is outlined in Scheme 1. The compounds used as initial starting materials in this invention may be purchased from commercial sources or alternatively are readily synthesized by standard procedures which are well know to those of ordinary skill in the art.

Some of the compounds of Formula I may exist as stereoisomers, and the invention includes all active stereoisomeric forms of these compounds. In the case of optically active isomers, such compounds may be obtained from corresponding optically active precursors using the procedures described above or by resolving racemic mixtures. The resolution may be carried out using various techniques such as chromatography, repeated recrystallization of derived asymmetric salts, or derivatization, which techniques are well known to those of ordinary skill in the art.

The compounds of the invention may be labeled in a variety of ways. For example, the compounds may contain radioactive isotopes such as, for example, $^3$H (tritium) and $^{14}$C (carbon-14). Similarly, the compounds may be advantageously joined, covalently or noncovalently, directly or through a linker molecule, to a wide variety of other compounds, which may provide pro-drugs or function as carriers, labels, adjuvents, coactivators, stabilizers, etc. Such labeled and joined compounds are contemplated within the present invention.

Analysis of Compounds

The subject compounds and compositions were demonstrated to have pharmacological activity in in vitro and in vivo assays, e.g., they are capable of specifically modulating a cellular physiology to reduce an associated pathology or provide or enhance a prophylaxis. Compounds and compositions of a particular embodiment of the invention are capable of specifically regulating LDL receptor gene expression. Compounds may be evaluated in vitro for their ability to increase LDL receptor expression using western-blot analysis, for example, as described by Tam et al. (*J. Biol.*

Chem. 1991, 266, 16764). Preferred such compounds and compositions provide $EC_{max}$ of less than about 50 µM, preferably less than about 5 µM, more preferably less than about 0.5 µM, more preferably less than about 0.05 µM, and most preferably less than about 0.005 µM in this assay (see, e.g. Example 28 herein). Established animal models to evaluate hypocholesterolemic effects of compounds are known in the art. For example, compounds disclosed herein are shown to lower cholesterol levels in hamsters fed a high-cholesterol diet, using a protocol similar to that described by Spady et al. (*J. Clin. Invest.* 1988, 81, 300), Evans et al. (*J. Lipid Res.* 1994, 35, 1634), and Lin et al (*J. Med. Chem.* 1995, 38, 277).

Compounds and compositions of a particular embodiment of the invention display specific toxicity to various types of cells, preferably exerting their cytotoxic effects by interacting with cellular tubulin, preferably covalently and irreversibly. Compounds and compositions may be evaluated in vitro for their ability to inhibit cell growth, for example, as described by Ahmed et al. (*J. Immunol. Methods* 1994, 170, 211). Preferred such compounds and compositions provide $IC_{50}$ of less than about 50 µM, preferably less than about 5 µM, more preferably less than about 0.5 µM, more preferably less than about 0.05 µM, and most preferably less than about 0.005 µM in this assay (see, e.g. Example 28 herein). Established animal models to evaluate antiproliferative effects of compounds are known in the art. For example, compounds can be evaluated for their ability to inhibit the growth of human tumors grafted into immunodeficient mice using methodology similar to that described by Rygaard and Povlsen (*Acta Pathol. Microbiol. Scand.* 1969, 77, 758) and Giovanella and Fogh (*Adv. Cancer Res.* 1985, 44, 69).

Formulation and Administration of Compounds and Pharmaceutical Compositions

The invention provides methods of using the subject compounds and compositions to treat disease or provide medicinal prophylaxis, to upregulate LDL receptor gene expression in a cell, to reduce blood cholesterol concentration in a host, to slow down and/or reduce the growth of tumors, etc. These methods generally involve contacting the cell with or administering to the host an effective amount of the subject compounds or pharmaceutically acceptable compositions.

The compositions and compounds of the invention and the pharmaceutically acceptable salts thereof can be administered in any effective way such as via oral, parenteral or topical routes. Generally, the compounds are administered in dosages ranging from about 2 mg up to about 2,000 mg per day, although variations will necessarily occur depending on the disease target, the patient, and the route of administration. Preferred dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day.

In one embodiment, the invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art.

The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other hypocholesterolemic or antiproliferative therapeutic or prophylactic agents, different from the subject compounds. In many instances, administration in conjunction with the subject compositions enhances the efficacy of such agents. Examplary antiproliferative agents include cyclophosphamide, methotrexate, adriamycin, cisplatin, daunomycin, vincristine, vinblastine, vinarelbine, paclitaxel, docetaxel, tamoxifen, flutamide, hydroxyurea, and mixtures thereof. Exemplary hypocholesterolemic and/or hypolipemic agents include: bile acid sequestrants such as quaternary amines (e.g. cholestyramine and colestipol); nicotinic acid and its derivatives; HMG-CoA reductase inhibitors such as mevastatin, pravastatin, and simvastatin; gemfibrozil and other fibric acids, such as gemfibrozil, clofibrate, fenofibrate, benzafibrate and cipofibrate; probucol; raloxifene and its derivatives; and mixtures thereof.

The compounds and compositions also find use in a variety of in vitro and in vivo assays, including diagnostic assays. For example, various allotypic LDL receptor gene expression processes may be distinguished in sensitivity assays with the subject compounds and compositions, or panels thereof. In certain assays and in in vivo distribution studies, it is desirable to used labeled versions of the subject compounds and compositions, e.g. radioligand displacement assays. Accordingly, the invention provides the subject compounds and compositions comprising a detectable label, which may be spectroscopic (e.g. fluorescent), radioactive, etc.

The following examples are offered by way of illustration and not by way of limitation.

EXAMPLES $^1$H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz. Electron Ionization (EI) mass spectra were recorded on a Hewlett Packard 5989A mass spectrometer. Mass spectrometry results are reported as the ratio of mass over charge, followed by the relative abundance of each ion (in parentheses).

Preparation of Synthetic Intermediates

Starting materials for the synthesis of the examples of the present invention are available from commercial sources, known in the art, e.g. *Organic Syntheses, Coll. Vol. VII*; 1990, Jeremiah P. Freeman, ed., John Wiley & Sons, 508–511; Robson, P., Smith, T. A., Stephens, R., Tatlow, J., *J. Chem. Soc.*, 1963, 3692–3703; and *Synthesis of Fluoroorganic Compounds*; 1985, Knunyants, I. and Yakobson, G., eds., Springer-Verlag, 190, and/or exemplified below:

Example A

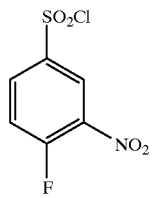

4-Fluoro-3-nitrophenylsulfonyl Chloride.

2-Fluoronitrobenzene (10.0 g, 70.9 mmol) was added to chlorosulfonic acid (10.0 ml, 150 mmol) at 65° C. After stirring at 85° C. for 18 h, the reaction mixture was cooled to room temperature and poured onto ice chips and extracted with $CH_2Cl_2$ (2×250 ml). The combined organic extracts were washed with saturated $NaHCO_3$ solution and dried ($MgSO_4$). Concentration at room temperature and then at 100° C. under high vacuum produced 2.40 g (14%) of the title compound as a yellow oil. $^1$H-NMR ($CDCl_3$): δ 8.76 (1H, dd, J=2.4, 6.5 Hz), 8.33 (1H, ddd, J=2.4, 3.8, 9.2 Hz), 7.61 (1H, t, J=9.2 Hz). MS (EI): 239 (15, M$^+$), 204 (100).

Example B

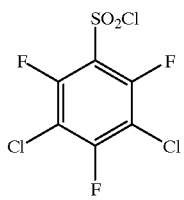

3,5-Dichloro-2,4,6-trifluorophenylsulfonyl Chloride.

1,3-Dichloro-2,4,6-trifluorobenzene (5.0 g, 25 mmol) and chlorosulfonic acid (10.0 ml, 150 mmol) were mixed at ambient temperature under a nitrogen atmosphere and the reaction was heated at 80° C. for 24 h. The mixture was then allowed to cool to ambient temperature and was poured onto 12 g of crushed ice. The product was extracted with diethyl ether, dried over $MgSO_4$, and evaporated to produce 4.9 g of the title compound, which was used without further purification. MS (EI): 300 (30, M$^+$), 298 (28), 263 (100), 199 (80).

Example C

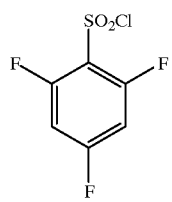

2,4,6-Trifluorophenylsulfonyl Chloride.

The title compound was synthesized from 1,3,5-trifluorobenzene by a method similar to that used in Example B. MS (EI): 230 (20, M$^+$), 195 (80), 131 (50), 81 (100).

Examples D and E

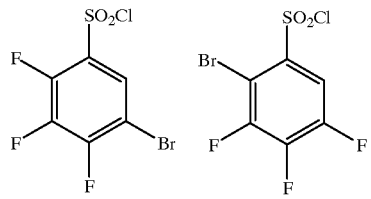

5-Bromo-2,3,4-trifluorophenylsulfonyl Chloride (Example D) and 2-Bromo-3,4,5-trifluorophenylsulfonyl Chloride (Example E).

The title compounds were obtained as a mixture from 1-bromo-2,3,4-trifluorobenzene by a method similar to that used in Example B.

Example F

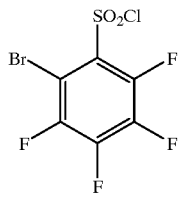

2-Bromo-3,4,5,6-tetrafluorophenylsulfonyl Chloride.

1Bromo-2,3,4,5-tetrafluorobenzene (5.0 g, 21.8 mmol) was mixed at ambient temperature with 20% fuming sulfuric acid (20 ml). The mixture was heated at 40° C. for 3 h and at 110° C. for 2 h. The reaction mixture was allowed to cool to ambient temperature and poured onto 12 g of crushed ice. The mixture was acidified dropwise with concentrated HCl (2 ml) until a solid, consisting mostly of 2-bromo-3,4,5,6-tetrafluorophenylsulfonic acid was formed. The solid was filtered, washed with 12N HCl, and dried under high vacuum to afford 5.3 g of 2-bromo-3,4,5,6-tetrafluorophenylsulfonic acid as a white hygroscopic solid that was used without further purification. To the sulfonic acid (3.0 g, 9.7 mmol) was then added phosphorous pentachloride (8.0 g, 38.4 mmol) in small portions, at ambient temperature (Caution: exothermic reaction with significant evolution of HCl). The reaction was allowed to stir for 20 minutes after the final addition of phosphorous pentachloride. The reaction mixture was then poured onto crushed ice and the white solid that formed was filtered and dried to afford 2.8 g of the title compound, which was used without further purification. MS (EI): 328 (30, M$^+$), 293 (70), 229 (30), 148 (100).

Example G

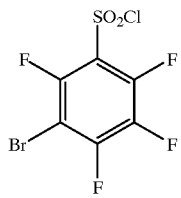

3-Bromo-2,4,5,6-tetrafluorophenylsulfonyl Chloride.

The title compound was synthesized from 1-bromo-2,3,4,6-tetrafluorobenzene by a method similar to that used in Example F. MS (EI): 328 (20, M$^+$), 293 (70), 229 (50), 148 (100).

Example H

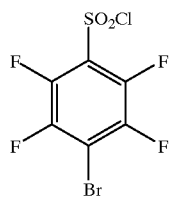

4-Bromo-2,3,5,6-tetrafluorophenylsulfonyl Chloride.

The title compound was synthesized from 1-bromo-2,3,5,6-tetrafluorobenzene by a method similar to that used in Example F. MS (EI): 328 (20, M+), 293 (70), 229 (50), 148 (100).

Example 1

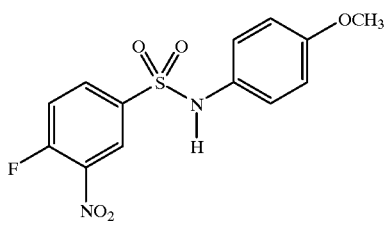

4-Fluoro-1-[(4-methoxyphenyl)aminosulfonyl]-3-nitrobenzene.

p-Anisidine (760 mg, 6.18 mmol) was added to a solution of 4-fluoro-3-nitrophenylsulfonyl chloride (740 mg, 3.09 mmol; Example A) in MeOH (10 ml) at ambient temperature. After stirring at room temperature for 15 min, the reaction mixture was concentrated under reduced pressure and the residue was taken up in ethyl acetate and filtered through a pad of silica gel. Concentration of the filtrate, followed by chromatography, provided 603 mg (60% yield) of the title compound. $^1$H-NMR (CDCl$_3$): δ 8.42 (1H, dd, J=2.3, 6.8 Hz), 7.88 (1H, ddd, J=2.4, 4.0, 8.8 Hz), 7.33 (1H, dd, J=8.8, 9.9 Hz), 6.98 (2H, m), 6.81 (2H, m), 6.45 (1H, s), 3.77 (3H, s). MS (EI): 326 (11, M+), 122 (100). Anal. Calcd. for C$_{13}$H$_{11}$FN$_2$O$_5$S: C, 47.85; H, 3.40; N, 8.59; S, 9.83. Found: C, 47.68; H, 3.44; N, 8.54; S, 9.88.

Example 2

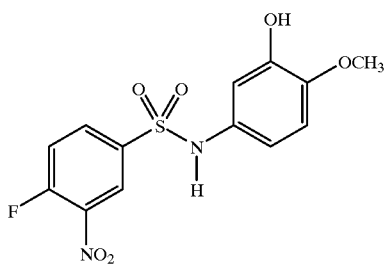

4-Fluoro-1-[(3-hydroxy-4-methoxyphenyl)aminosulfonyl]-3-nitrobenzene.

The title compound was prepared in a manner similar to that described in Example 1, by replacing p-anisidine with 3-hydroxy-4-methoxyaniline. $^1$H-NMR (CDCl$_3$): δ 8.41 (1H, dd, J=2.4, 6.7 Hz), 7.92 (1H, m), 7.14 (1H, ddd, J=2.4, 4.0, 9.0 Hz), 7.35 (1H, dd, J=9.6, 9.0 Hz), 6.72 (1H, d, J=8.5 Hz), 6.62 (1H, d, J=2.5 Hz), 6.58 (1H, dd, J=2.5, 8.5 Hz), 6.44 (1H, s), 5.64 (1H, s), 3.85 (3H, s). Anal. Calcd. for C$_{13}$H$_{11}$FN$_2$O$_6$S: C, 45.62; H, 3.24; N, 8.18; S, 9.37. Found: C, 45.71; H, 3.25; N, 8.17; S, 9.29.

Example 3

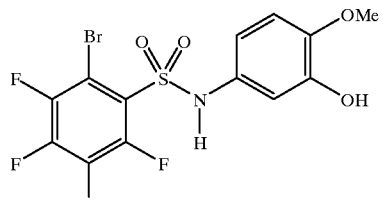

1-Bromo-3,4,5,6-tetrafluoro-2-[(3-hydroxy-4-methoxyphenyl)aminosulfonyl]benzene.

The title compound was prepared in a manner similar to that described in Example 1 by replacing p-anisidine with 3-hydroxy-4-methoxyaniline and replacing 4-fluoro-3-nitrophenylsulfonyl chloride with 2-bromo-3,4,5,6-tetrafluorophenylsulfonyl chloride (Example F). $^1$H-NMR (CDCl$_3$): δ 7.28 (br s, 1H), 6.69 (m, 3H), 5.72 (s, 1H), 3.82 (s, 3H). MS (EI): 431 (20), 429 (20), 138 (100). Anal. Calcd. for C$_{13}$H$_8$BrF$_4$NO$_4$S: C, 36.30; H, 1.87; N, 3.26; S, 7.45. Found: C, 36.20; H, 1.90; N, 3.31; S, 7.39.

Example 4

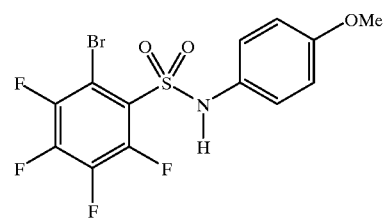

1-Bromo-3,4,5,6-tetrafluoro-2-[(4-methoxyphenyl)aminosulfonyl]benzene.

The title compound was prepared in a manner similar to that described in Example 1 by replacing 4-fluoro-3-nitrophenylsulfonyl chloride with 2-bromo-3,4,5,6-tetrafluorophenylsulfonyl chloride (Example F). $^1$H-NMR (CDCl$_3$): δ 7.23 (1H, br s), 7.07 (2H, dd, J=9.0 and 2.0 Hz), 6.78 (2H, dd, J=9.0 and 2.0 Hz), 3.75 (3H, s). MS (EI): 415/413 (10, M+), 122 (100). Anal. Calcd. for C$_{13}$H$_8$BrF$_4$NO$_3$S: C, 37.70; H, 1.95; N, 3.38; S, 7.74. Found: C, 37.60; H, 1.92; N, 3.30; S, 7.71.

Example 5

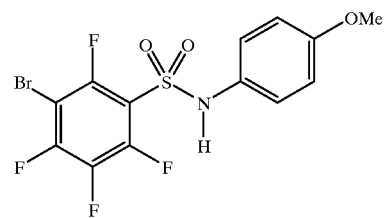

1-Bromo-2,4,5,6-tetrafluoro-3-[(4-methoxyphenyl)aminosulfonyl)]benzene.

The title compound was prepared in a manner similar to that described in Example 1 by replacing 4-fluoro-3- nitrophenylsulfonyl chloride with 3-bromo-2,4,5,6-tetrafluorophenylsulfonyl chloride (Example G). $^1$H-NMR (CDCl$_3$): δ 7.10 (2H, dd, J=9.0 and 2.0 Hz), 7.07 (1H, br s), 6.82 (2H, dd, J=9.0 and 2.0 Hz), 3.77 (3H, s). MS(EI): 415/413 (10, M$^+$), 122 (100). Anal. Calcd. for C$_{13}$H$_8$BrF$_4$NO$_3$S: C, 37.70; H, 1.95; N, 3.38; S, 7.74. Found: C, 37.66; H, 1.94; N, 3.33; S, 7.67.

Example 6

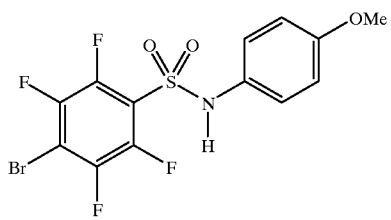

1-Bromo-2,3,5,6-tetrafluoro-4-[(4-methoxyphenyl)aminosulfonyl]benzene.

The title compound was prepared in a manner similar to that described in Example 1 by replacing 4-fluoro-3-nitrophenylsulfonyl chloride with 4-bromo-2,3,5,6-tetrafluorophenylsulfonyl chloride (Example H). $^1$H-NMR (CDCl$_3$): δ 7.16 (1H, br s), 7.11 (2H, dd, J=9.0 and 2.0 Hz), 6.82 (2H, dd, J=9.0 and 2.0 Hz), 3.77 (3H, s). MS(EI) 415/413 (10, M$^+$), 122 (100). Anal. Calcd. for C$_{13}$H$_8$BrF$_4$NO$_3$S: C, 37.70; H, 1.95; N, 3.38; S, 7.74. Found: C, 37.62; H, 1.95; N, 3.34; S, 7.66.

Example 7

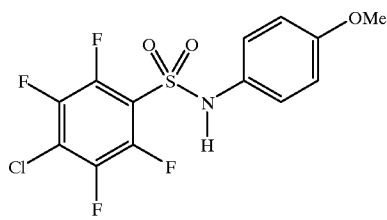

1-Chloro-2,3,5,6-tetrafluoro-4-[(4-methoxyphenyl)aminosulfonyl]benzene.

The title compound was prepared in a manner similar to that described in Example 1 by replacing 4-fluoro-3-nitrophenylsulfonyl chloride with 4-chloro-2,3,5,6-tetrafluorophenylsulfonyl chloride. $^1$H-NMR (CDCl$_3$): δ 7.12 (2H, d, J=9.0 Hz), 6.90 (1H, br s), 6.83 (2H, J=9.0 Hz), 3.78 (3H, s). MS(EI): 369 (20, M$^+$), 122 (100).

Example 8

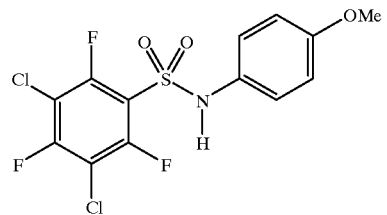

1,3-Dichloro-2,4,6-trifluoro-5-[(4-methoxyphenyl)aminosulfonyl]benzene.

The title compound was prepared in a manner similar to that described in Example 1 by replacing 4-fluoro-3-nitrophenylsulfonyl chloride with 3,5-dichloro-2,4,6-trifluorophenylsulfonyl chloride (Example B). $^1$H-NMR (CDCl$_3$): δ 7.09 (2H, d, J=9.0 Hz), 6.85 (1H, br s), 6.82 (2H, d, J=9.0 Hz), 3.77 (3H, s). MS (EI): 386 (15, M$^+$), 385 (20), 122 (100). Anal. Calcd. for C$_{13}$H$_8$Cl$_2$F$_3$NO$_3$S: C, 40.43; H, 2.09; N, 3.63; S, 8.30. Found: C, 40.34; H, 2.06; N, 3.70; S, 8.22.

Example 9

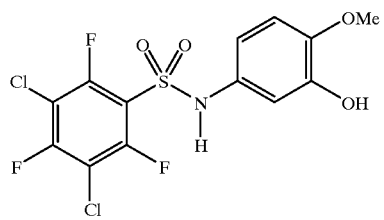

1,3-Dichloro-2,4,6-trifluoro-5-[(3-hydroxy-4-methoxyphenyl)aminosulfonyl]benzene.

The title compound was prepared in a manner similar to that described in Example 1 by replacing p-anisidine with 3-hydroxy-4-methoxyaniline and replacing 4-fluoro-3-nitrophenylsulfonyl chloride with 3,5-dichloro-2,4,6-trifluorophenylsulfonyl chloride (Example B). $^1$H-NMR (CDCl$_3$): δ 6.88 (1H, br s), 6.7–6.8 (3H, m), 5.66 (1H, s), 3.85 (3H, s). MS(EI): 402 (15, M$^+$), 401 (20), 138 (100). Anal. Calcd. for C$_{13}$H$_8$Cl$_2$F$_3$NO$_4$S: C, 38.83; H, 2.00; N, 3.48; S, 7.97. Found: C, 38.66; H, 1.97; N, 3.39; S, 7.86.

Example 10

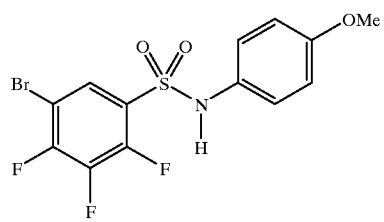

1-Bromo-2,3,4-trifluoro-5-[(4-methoxyphenyl)aminosulfonyl]benzene.

1-Bromo-2,3,4-trifluoro-5-[(4-methoxyphenyl)aminosulfonyl]benzene (Example 10) and 1-Bromo-4,5,6-trifluoro-2-[(4-methoxyphenyl)aminosulfonyl]benzene (Example 11) were prepared in a manner similar to that described in Example 1 by replacing 4-fluoro-3-nitrophenylsulfonyl chloride with a mixture of 5-bromo-2,3,4-trifluorophenylsulfonyl chloride (Example D) and 2-bromo-3,4,5-trifluorophenylsulfonyl chloride (Example E). The two isomeric compounds were separated by column chromatography (silica gel; ethyl acetate:hexanes, 1:4). $^1$H-NMR (CDCl$_3$): δ 7.76 (1H, m), 7.04 (2 H; d, J=9.0 Hz), 6.82 (1H, br s), 6.80 (2H, d, J=9.0 Hz), 3.75 (3H, s). MS(EI): 397/395 (20, M$^+$), 122 (100). Anal. Calcd. for C$_{13}$H$_9$BrF$_3$NO$_3$S: C, 39.41; H, 2.29; N, 3.54; S, 8.08. Found: C, 39.34; H, 2.23; N, 3.47; S, 7.99.

Example 11

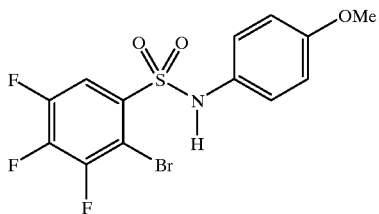

1-Bromo-4,5,6-trifluoro-2-[(4-methoxyphenyl)aminosulfonyl]benzene.

$^1$H-NMR (CDCl$_3$): δ 7.69 (1H, m), 7.08 (1H, br s), 7.03 (2H, dd, J=9.0 and 2.0 Hz), 6.76 (2H, dd, J=9.0 and 2.0 Hz), 3.75 (3H, s). MS(EI): 397/395 (20, M$^+$), 122 (100). Anal. Calcd. for C$_{13}$H$_9$BrF$_3$NO$_3$S: C, 39.41; H, 2.29; N, 3.54; S, 8.08. Found: C, 39.32; H, 2.31; N, 3.44; S, 7.99.

Example 12

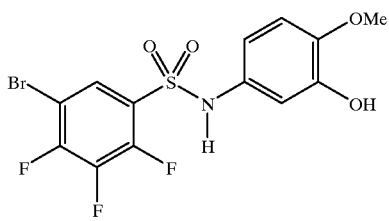

1-Bromo-2,3,4-trifluoro-5-[(3-hydroxy-4-methoxyphenyl)aminosulfonyl]benzene.

1-Bromo-2,3,4-trifluoro-5-[(3-hydroxy-4-methoxyphenyl)aminosulfonyl]benzene (Example 12) and 1-Bromo-4,5,6-trifluoro-2-[(3-hydroxy-4-methoxyphenyl)aminosulfonyl]benzene (Example 13) were prepared in a manner similar to that described in Example 1 by replacing 4-fluoro-3-nitrophenylsulfonyl chloride with a mixture of 5-bromo-2,3,4-trifluorophenylsulfonyl chloride (Example D) and 2-bromo-3,4,5-trifluorophenylsulfonyl chloride (Example E) and replacing p anisidine with 3-hydroxy-4-methoxyaniline. The two isomeric compounds were separated by column chromatography (silica gel; ethyl acetate:hexanes, 1:4). $^1$H-NMR (CDCl$_3$): δ 7.79 (1H, m), 6.72–6.62 (4H, m), 5.65 (1H, s), 3.85 (3H, s).

Example 13

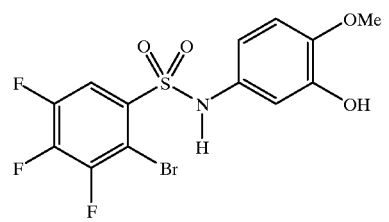

1-Bromo-4,5,6-trifluoro-2-[(3-hydroxy-4-methoxyphenyl)aminosulfonyl]benzene.

$^1$H-NMR (CDCl$_3$): δ 7.73 (1H, m), 6.94 (1H, br s), 6.72–6.62 (3H, m), 5.63 (1H, s), 3.83 (3H, s).

Example 14

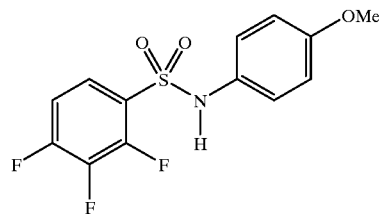

2,3,4-Trifluoro-1-[(4-methoxyphenyl)aminosulfonyl]benzene.

The title compound was prepared in a manner similar to that described in Example 1 by replacing 4-fluoro-3-nitrophenylsulfonyl chloride with 2,3,4-trifluorophenylsulfonyl chloride. $^1$H-NMR (CDCl$_3$): δ 7.51 (1H, m), 7.02 (3H, m), 6.78 (2H, dd, J=9.0 and 2.0 Hz), 6.65 (1H, br s), 3.76 (3H, s). MS(EI): 317 (20, M$^+$), 122 (100). Anal. Calcd. for C$_{13}$H$_{10}$F$_3$NO$_3$S: C, 49.21; H, 3.18; N, 4.41; S, 10.10. Found: C, 49.10; H, 3.14; N, 4.32; S, 9.99.

Example 15

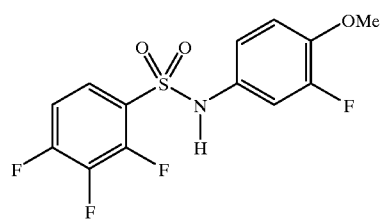

2,3,4-Trifluoro-1-[(3-Fluoro-4-methoxyphenyl)aminosulfonyl]ybenzene.

The title compound was prepared in a manner similar to that described in Example 1, by replacing 4-fluoro-3-nitrophenylsulfonyl chloride with 2,3,4-trifluorophenylsulfonyl chloride and replacing p-anisidine with 3-fluoro-4-methoxyaniline. $^1$H-NMR (CDCl$_3$): δ 7.52 (1H, m), 7.00 (1H, m), 6.93 (1H, m), 6.80 (2H, m), 6.70 (1H, br s), 3.80 (3H, s).

Example 16

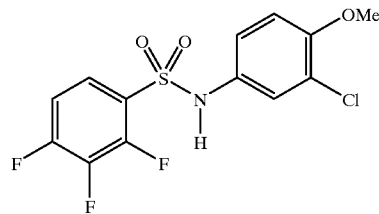

1-[(3-Chloro-4-methoxyphenyl)aminosulfonyl]-2,3,4-trifluorobenzene.

The title compound was prepared in a manner similar to that described in Example 1 by replacing 4-fluoro-3-nitrophenylsulfonyl chloride with 2,3,4-trifluorophenylsulfonyl chloride and replacing p-anisidine with 3-chloro-4-methoxyaniline. $^1$H-NMR (CDCl$_3$): δ 7.56 (1H, m), 7.17 (1H, d, J=2.0 Hz), 7.02 (1H, m), 6.98 (1H, dd, J=9.0 and 2.0 Hz), 6.78 (1H, d, J=9.0 Hz), 6.72 (1H, br s), 3.83 (3H, s). MS(EI): 352 (7, M$^+$), 351 (20), 156 (100). Anal. Calcd. for C$_{13}$H$_9$ClF$_3$NO$_3$S: C, 44.39; H, 2.58; N, 3.98; S. 9.11. Found: C, 44.31; H, 2.58; N, 3.96; S, 9.08.

Example 17

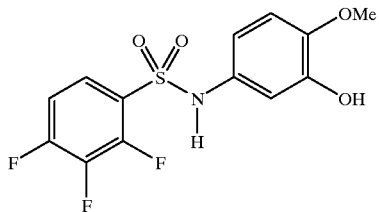

1-[(3-Hydroxy-4-methoxyphenyl)aminosulfonyl]-2,3,4-trifluorobenzene.

The title compound was prepared in a manner similar to that described in Example 1 by replacing 4-fluoro-3-nitrophenylsulfonyl chloride with 2,3,4-trifluorophenylsulfonyl chloride and replacing p-anisidine with 3-hydroxy-4-methoxyaniline. $^1$H-NMR (CDCl$_3$): δ 7.55 (1H, m), 7.00 (1H, m), 6.70 (2H, m), 6.60 (2H, m), 5.61 (1H, s), 3.83 (3H, s). Anal. Calcd. for C$_{13}$H$_{10}$F$_3$NO$_4$S: C, 46.85; H, 3.02; N, 4.20; S, 9.62. Found: C, 46.79; H, 3.03; N, 4.24; S, 9.53.

Example 18

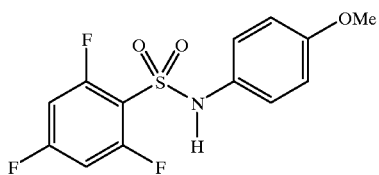

2,4,6-Trifluoro-1-[(4-methoxyphenyl)aminosulfonyl]benzene.

The title compound was prepared in a manner similar to that described in Example 1 by replacing 4-fluoro-3-nitrophenylsulfonyl chloride with 2,4,6-trifluorophenylsulfonyl chloride (Example C). $^1$H-NMR (CDCl$_3$): δ 7.08 (2H, dd, J=9.0 and 2.0 Hz), 6.8–6.7 (5H, m), 3.75 (3H, s). Anal. Calcd. for C$_{13}$H$_{10}$F$_3$NO$_3$S: C, 49.21; H, 3.18; N, 4.41; S, 10.10. Found: C, 49.13; H, 3.20; N, 4.39; S, 10.01.

Example 19

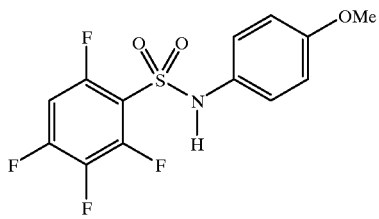

2,3,4,6-Tetrafluoro-1-[(4-methoxyphenyl)aminosulfonyl]benzene.

1-Bromo-2,4,5,6-tetrafluoro-3-[(4-methoxyphenyl)aminosulfonyl]benzene (250 mg, 0.6 mmol) (Example 5) was dissolved in methanol (25 ml) and placed in a closed vessel. A catalytic amount of 10% Pd/charcoal (25 mg) was added and the mixture was hydrogenated at 60 psi H$_2$ for 4 h. The mixture was filtered through celite, the solvent was evaporated and the residue was purified by chromatography (silica; EtOAc/Hexane, 1:4) to yield 82 mg of the title compound. $^1$H-NMR (CDCl$_3$): δ 7.10 (2H, dd, J=9.0 and 2.0 Hz), 6.94 (1H, br s), 6.85 (1H, m). 6.79 (2H, dd, J=9.0 and 2.0 Hz), 3.75 (3H, s). MS(EI): 335 (20, M$^+$), 122 (100). Anal. Calcd. for C$_{13}$H$_9$F$_4$NO$_3$S: C, 46.57; H, 2.71; N, 4.18; S, 9.56. Found: C, 46.46; H, 2.67; N, 4.17; S, 9.52.

Example 20

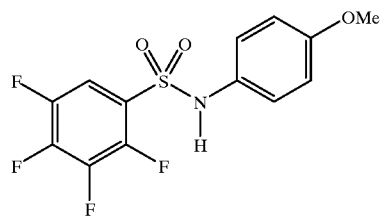

2,3,4,5-Tetrafluoro-1-[(4-methoxyphenyl)aminosulfonyl]benzene.

The title compound was prepared in a manner similar to that described in Example 19 by replacing 1-bromo-2,4,5,6-tetrafluoro-3-[(4-methoxyphenyl)aminosulfonyl]benzene with 1-bromo-3,4,5,6-tetrafluoro-2-[(4-methoxyphenyl)aminosulfonyl]benzene (Example 4). $^1$H-NMR (CDCl$_3$): δ 7.40 (1H, m), 7.05 (2H, dd, J=9.0 and 2.0 Hz), 6.80 (2H, dd, J=9.0 and 2.0 Hz), 3.76 (3H, s). MS(EI): 335 (20, M$^+$), 122 (100). Anal. Calcd. for C$_{13}$H$_9$F$_4$NO$_3$S: C, 46.57; H, 2.71; N, 4.18; S, 9.56. Found: C, 46.44; H, 2.67; N, 4.13; S, 9.47.

Example 21

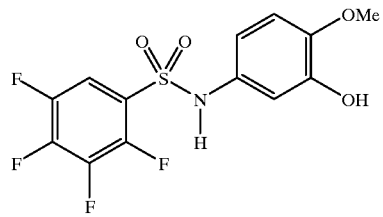

2,3,4,5-Tetrafluoro-1-[(3-hydroxy-4-methoxyphenyl)aminosulfonyl]benzene.

The title compound was prepared in a manner similar to that described in Example 19 by replacing 1-bromo-2,4,5,6-tetrafluoro-3-[(4-methoxyphenyl)aminosulfonyl]benzene with 1-bromo-3,4,5,6-tetrafluoro-2-[(3-hydroxy-4-methoxyphenyl)aminosulfonyl]benzene (Example 3). $^1$H-NMR (CDCl$_3$): δ 7.43 (1H, m), 6.80 (1H, br s), 6.73–6.60 (3H, m), 5.67 (1H, s), 3.84 (3H, s). MS(EI): 351(20, M$^+$), 138 (100). Anal. Calcd. for C$_{13}$H$_9$F$_4$NO$_4$S: C, 44.45; H, 2.58; N, 3.99; S, 9.13. Found: C, 44.39; H, 2.59; N, 3.94; S, 9.24.

Example 22

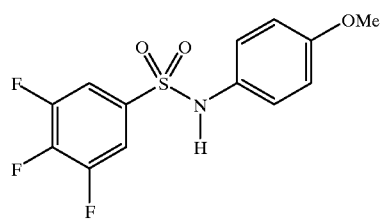

3,4,5-Trifluoro-1-[(4-methoxyphenyl)aminosulfonyl]benzene.

The title compound was prepared in a manner similar to that described in Example 19 by replacing 1-bromo-2,4,5,6-tetrafluoro-3-[(4-methoxyphenyl)aminosulfonyl]benzene with 1-bromo-4,5,6-trifluoro-2-[(4-methoxyphenyl)aminosulfonyl]benzene (Example 11). $^1$H-NMR (CDCl$_3$): δ 7.35 (2H, t, J=6.0 Hz), 7.00 (2H, d, J=9.0 Hz), 6.81 (2H, d, J=9.0 Hz), 3.78 (3H, s). MS(EI) 317 (20, M$^+$), 122 (100). Anal. Calcd. for C$_{13}$H$_{10}$F$_3$NO$_3$S: C, 49.21; H, 3.18; N, 4.41; S, 10.10. Found: C, 49.09; H, 3.15; N, 4.37; S, 10.03.

Example 23

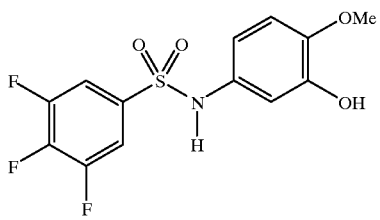

3,4,5-Trifluoro-1-[(3-hydroxy-4-methoxyphenyl)aminosulfonyl]benzene.

The title compound was prepared in a manner similar to that described in Example 19 by replacing 1-bromo-2,4,5,6-tetrafluoro-3-[(4-methoxyphenyl)aminosulfonyl]benzene with 1-bromo-4,5,6-trifluoro-2-[(3-hydroxy-4-methoxyphenyl)aminosulfonyl]benzene (Example 13). $^1$H-NMR (CDCl$_3$): δ 7.38 (2H, t, J=6.0 Hz), 6.74 (1H, d, J=9.0 Hz), 6.64 (1H, d, J=2.0 Hz), 6.58 (1H, dd, J=9.0 and 2.0 Hz), 5.64 (1H, s), 3.88 (3H, s). Anal. Calcd. for C$_{13}$H$_{10}$F$_3$NO$_4$S: C, 46.85; H, 3.02; N, 4.20; S, 9.62. Found: C, 46.75; H, 3.01; N, 4.20; S, 9.56.

Example 24

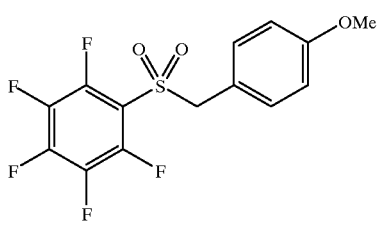

4-Methoxybenzyl Pentafluorophenyl Sulfone.

To a solution of 4-methoxybenzylbromide (2.00 g, 9.95 mmol) in DMF (20 ml) at room temperature was added potassium carbonate (2.07 g, 15.0 mmol) followed by pentafluorothiophenol (1.33 ml, 9.97 mmol). After stirring at room temperature for 1 h, the reaction mixture was poured onto water and extracted with diethyl ether. The combined organic extracts were washed with 1 M NaOH, dried and concentrated to give a white solid which was used directly in the next step. The sulfide (1.11 g, 3.47 mmol) was dissolved in dichloromethane (20 ml) and cooled to 0° C. m-chloroperbenzoic acid, MCPBA, (1.20 g, 6.95 mmol) was added and the resulting mixture stirred at room temperature for 2 h. The reaction mixture was poured onto 1 M NaOH (50 ml) and extracted with dichloromethane (3×25 ml). The combined organic extracts were washed with brine, dried (MgSO$_4$), concentrated and flash chromatographed (25:25:1, 20:20:3/hexanes:dichloromethane:ethyl acetate) to provide 413 mg (34%) of the title compound as a white solid. $^1$H NMR (CDCl$_3$): d 7.18–7.22 (2H, m), 6.85–6.80 (2H, m), 4.48 (2H, s), 3.78 (3H, s). MS (EI): m/z 352 (2, M$^+$), 121 (100). Anal Calcd. for C$_{14}$H$_9$F$_5$O$_3$S: C, 47.73; H, 2.58; S, 9.10. Found: C, 47.88; H, 2.66; S, 8.97.

Example 25

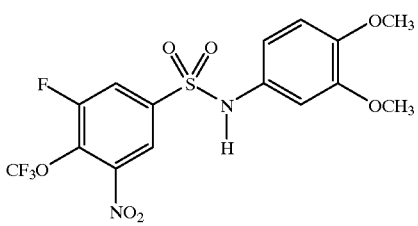

1-[(3,4-Dimethoxyphenyl)aminosulfonyl]-3-fluoro-5-nitro-4-trifluoromethoxy-benzene.

3,4-Dimethoxyaniline (1.53 g, 10 mmol) is added to a solution of 3-fluoro-5-nitro-4-trifluoromethoxyphenylsulfonyl chloride (2.87 g, 12 mmol) in MeOH (20 ml) at ambient temperature. After stirring at room temperature for 15 min, the reaction mixture is concentrated under reduced pressure and the residue is taken up in ethyl acetate and filtered through a pad of silica gel. Concentration of the filtrate, followed by chromatography, provides the title compound.

Example 26

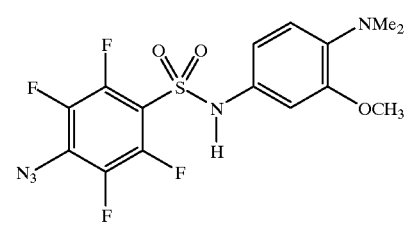

4-Azido-1-[(4-dimethylamino-3-methoxyphenyl)aminosulfonyl]-2,3,5,6-tetrafluoro-benzene.

4-Dimethylamino-3-methoxyaniline (1.66 g, 10 mmol) is added to a solution of 4-azido-2,3,5,6-tetrafluorophenylsulfonyl chloride (3.47 g, 12 mmol) in MeOH (20 ml) at ambient temperature. After stirring at room temperature for 15 min, the reaction mixture is concentrated under reduced pressure and the residue is taken up in ethyl acetate and filtered through a pad of silica gel. Concentration of the filtrate, followed by chromatography, provides the title compound.

Example 27

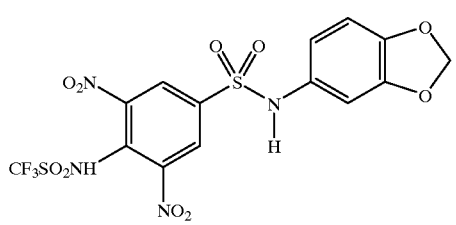

3,5-dinitro-1-[(3,4-methylenedioxyphenyl)aminosulfonyl]-4-(trifluoromethylsulfonamido)benzene 3,4-Methylenedioxyaniline (1.37 g, 10 mmol) is added to a solution of 3,5-dinitro-4-(trifluoromethylsulfonamido)phenyisulfonyl chloride (4.96 g, 12 mmol) in MeOH (20 ml)

at ambient temperature. After stirring at room temperature for 15 min, the reaction mixture is concentrated under reduced pressure and the residue is taken up in ethyl acetate and filtered through a pad of silica gel. Concentration of the filtrate, followed by chromatography, provides the title compound.

Example 28
Assessment of Biological Activity.

Compounds were evaluated for their ability to inhibit in vitro the growth of HeLa cells, an immortal cell line derived from a human cervical carcinoma commonly used to evaluate the cytotoxicity of potential therapeutic agents. The following data reflect the cytotoxicity of selected examples of the present invention. The values given represent the concentration of test compound required to inhibit by 50% the uptake of Alamar Blue (Biosource International, Camarillo, Calif.) by HeLA cell cultures, which correlates directly with the overall levels of cellular metabolism in the culture, and is generally accepted as an appropriate marker of cell growth. The test was conducted according to the method of Ahmed et al. (*J. Immunol. Methods* 1994, 170, 211). The following selected examples display potent cytotoxic activity in this assay, with $IC_{50}$ values ranging from 0.05 µM to 5.0 µM.

| Compound | IC50 (µM) |
|---|---|
| Example 2 | 0.15 |
| Example 3 | 0.05 |
| Example 4 | 0.15 |
| Example 5 | 0.15 |
| Example 6 | 5.0 |
| Example 7 | 1.5 |
| Example 8 | 0.15 |
| Example 9 | 0.05 |
| Example 10 | 0.5 |
| Example 11 | 0.5 |
| Example 17 | 1.5 |
| Example 19 | 5.0 |
| Example 20 | 0.5 |
| Example 21 | 0.15 |
| Example 22 | 5.0 |
| Example 23 | 1.5 |
| Example 24 | 5.0 |

Certain compounds were evaluated for their ability to increase LDL receptor expression in HepG2 cells using western-blot analysis as described by Tam et al., (*J. Biol. Chem.*, 1991, 266, 16764). The data presented ($EC_{max}$) reflect the minimum concentration at which a maximal induction of LDL receptor levels was observed for each compound. In all cases, the level of induction was greater than that observed under lipid-free conditions (activated system) in the absence of the test compounds.

| Compound | $EC_{max}$ (µm) |
|---|---|
| Example 1 | 5 |
| Example 2 | 1.5 |
| Example 3 | 0.15 |
| Example 4 | 0.5 |
| Example 5 | 0.5 |
| Example 6 | 50 |
| Example 7 | 50 |
| Example 8 | 0.5 |
| Example 9 | 0.15 |
| Example 10 | 1.5 |

| Compound | $EC_{max}$ (µm) |
|---|---|
| Example 11 | 1.5 |
| Example 19 | 15 |
| Example 20 | 1.5 |
| Example 21 | 0.5 |
| Example 22 | 5 |
| Example 24 | 1.5 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

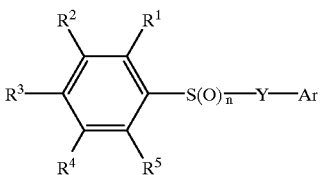

or a pharmaceutically acceptable salt thereof, wherein:
n is 2;
$R^1$ is a member selected from the group consisting of hydrogen, (C1–C6) alkyl, halogen, $OCF_3$, $CF_3$, $NO_2$, CN, and $CO_2$—$R^8$;
$R^2$ is a member selected from the group consisting of $NO_2$, CN, $CO_2$—$R^8$ and $SO_2$—$R^8$;
$R^3$ is a member selected from the group consisting of halogen and $OCF_3$;
$R^4$ is a member selected from the group consisting of hydrogen, halogen, $OCF_3$, $CF_3$, $NO_2$, CN, and $CO_2$—$R^8$;
$R^5$ is a member selected from the group consisting of hydrogen, (C1–C6) alkyl, halogen, $OCF_3$, $CF_3$, $NO_2$, CN, and $CO_2$—$R^8$;
Y is $N(R^9)$;
wherein $R^6$ and $R^7$ are each independently selected from the group consisting of hydrogen, (C1–C6) alkyl and (C2–C6) heteroalkyl; $R^8$ is selected from the group consisting of (C1–C6) alkyl and (C2–C6) heteroalkyl; and $R^9$ is selected from the group consisting of hydrogen, substituted or unsubstituted (C1–C10)alkyl, substituted or unsubstituted (C3–C6)alkenyl, substituted or unsubstituted (C2–C6)heteroalkyl, substituted or unsubstituted (C3–C6)heteroalkenyl, substituted or unsubstituted (C3–C6)alkynyl, substituted or unsubstituted (C3–C8)cycloalkyl; and
Ar is a substituted or unsubstituted phenyl group,
wherein said substituents are independently selected from the group consisting of OH, halogen, $NH_2$, $NH(C1-C6)alkyl$, $N((C1-C6)alkyl)_2$, (C1–C6) alkyl, and (C1–C6)alkoxy.

2. The compound of claim 1, wherein $R^3$ is halogen.

3. The compound of claim 2, wherein $R^4$ is selected from the group consisting of hydrogen, F, Cl, Br, $OCF_3$, $CF_3$, $NO_2$, and CN.

4. The compound of claim 3, wherein $R^3$ is F, Cl or Br.

5. The compound of claim 4, wherein $R^3$ is F.

6. The compound of claim 5, wherein $R^2$ is selected from the group consisting of $NO_2$, CN, and $CO_2$—$R^8$.

7. The compound of claim 6, wherein $R^4$ is selected from the group consisting of hydrogen, F, Cl, Br, $OCF_3$ and $CF_3$.

8. The compound of claim 4, wherein $R^3$ is Cl.

9. The compound of claim 8, wherein $R^2$ is selected from $NO_2$, CN, and $CO_2$—$R^8$.

10. The compound of claim 9, wherein $R^4$ is selected from the group consisting of are independently selected from F, Cl, Br, $OCF_3$.

11. The compound of claim 4, wherein $R^3$ is Br.

12. The compound of claim 11, wherein $R^2$ is selected from $NO_2$, CN, and $CO_2$—$R^8$.

13. The compound of claim 12, wherein $R^4$ is a member selected from the group consisting of F, Cl, Br, $OCF_3$ and $CF_3$.

14. The compound of claim 11, wherein $R^3$ is $OCF_3$.

15. The compound of claim 14, wherein $R^2$ is selected from $NO_2$, CN and $CO_2$—$R^8$.

16. The compound of claim 15, wherein $R^2$ and $R^4$ are independently selected from F, Cl, Br, $OCF_3$ and $CF_3$.

* * * * *

UNITED STATES PATENT AND TRADEMARK OFFICE
CERTIFICATE OF CORRECTION

PATENT NO.     : 6,284,923 B1
DATED          : September 4, 2001
INVENTOR(S)    : Julio Cesar Medina et al.

It is certified that error appears in the above-identified patent and that said Letters Patent is hereby corrected as shown below:

Title page, Item [54] and Column 1, line 3,
Change the word in the title from "ACTION" to -- AGENTS -- so that the title reads:
-- SUBSTITUTED BENZENE COMPOUNDS AS ANTIPROLIFERATIVE AND CHOLESTEROL LOWERING AGENTS --

Column 41,
Line 57, delete "μm" and insert -- μM --.

Column 42,
Line 4, delete "μm" and insert -- μM --.
Line 51, delete "$R^6$ and $R^7$ are each independently selected from the group consisting of hydrogen, (C1-C6) alkyl and (C2-C6) heteroalkyl;"
Line 58, after "alkenyl," delete "subsituted" and insert -- substituted --.

Column 43,
Line 15, after "consisting of", delete "are independently selected from"

Signed and Sealed this

Twenty-ninth Day of April, 2003

JAMES E. ROGAN
*Director of the United States Patent and Trademark Office*